United States Patent [19]

Swart et al.

[11] Patent Number: 6,147,120

[45] Date of Patent: Nov. 14, 2000

[54] SYNERGISTIC ANTIMICROBIAL SKIN WASHING COMPOSITIONS

[75] Inventors: Sally K. Swart, Inver Grove Heights; John Hilgren, Shorview; William Feil, Hastings; Mary Bennett, Eagan, all of Minn.

[73] Assignee: Ecolab Inc., St. Paul, Minn.

[21] Appl. No.: 09/251,271

[22] Filed: Feb. 16, 1999

[51] Int. Cl.[7] .................. A61K 31/075; A61K 31/27; A61K 31/05
[52] U.S. Cl. ................. 514/721; 514/482; 514/731
[58] Field of Search ............... 424/65; 514/859, 514/863, 553, 546, 568, 557, 721, 482, 731

[56] References Cited

U.S. PATENT DOCUMENTS

| | | | |
|---|---|---|---|
| 5,124,355 | 6/1992 | Tully et al. | 514/526 |
| 5,374,536 | 12/1994 | Robertson | 435/26 |
| 5,512,199 | 4/1996 | Khan et al. | 510/131 |
| 5,569,461 | 10/1996 | Andrews | 424/405 |
| 5,611,938 | 3/1997 | Smolik et al. | 210/755 |
| 5,614,538 | 3/1997 | Nelson, Jr. | 514/345 |
| 5,641,808 | 6/1997 | Gaffney et al. | 514/526 |
| 5,736,574 | 4/1998 | Burnier et al. | 514/568 |
| 5,741,757 | 4/1998 | Cooper et al. | 504/153 |
| 5,776,960 | 7/1998 | Oppong et al. | 514/345 |
| 5,874,071 | 2/1999 | Yu et al. | 424/65 |

*Primary Examiner*—Theodore J. Criares
*Assistant Examiner*—Vickie Kim
*Attorney, Agent, or Firm*—Merchant & Gould

[57] ABSTRACT

A synergistic composition and a synergistic system for use in treating the skin and hair of people and animals comprises separate treatment compositions (solution, dispersions, emulsions, suspensions or other liquid or liquefiable materials). One treatment with a first composition that may comprise at least 0.1% by weight of antimicrobially active aliphatic phenol derivative and treatment with another composition being selected from the group consisting of:

a) a solution comprising an antimicrobially active cationic species;

b) a comprising antimicrobially active aliphatic phenol derivative, preferably in a different weight percentage of antimicrobially active aliphatic phenol derivative than said one composition, comprising greater than 0.3% antimicrobially active aliphatic phenol derivative;

c) a solution comprising an alcohol provides a synergistic antimicrobial action. These compositions do not have to be applied in any particular order, and more than two compositions may be combined in separate or sequential applications. The single compositions of the present invention comprise, for example, a single composition comprising at least 0.1% by weight Triclosan and at least one synergistic additive selected from the group consisting of chlorhexidene gluconate, solutions with greater than 0.3% Triclosan and an alcohol. These compositions, both as single compositions or as separate compositions have been found to provide synergistic antimicrobial effects. It is surprising that even when the separate compositions are applied with significant periods of time between application of the individual compositions (e.g., 2, 3, 5 or even 8 hours between applications) a synergistic effect may be provided. This is believed to be at least in part because some of the materials may persist on the skin and later would be combined with the application of the other synergistic composition. Because of the unique ability to provide synergy in separate compositions, with gaps in time between application of the separate materials, a system of washing, cleansing, lubricating, and moisturizing compositions may be provided within a health care complex. In this manner, as an individual applies the various compositions over the course of the day, due to varying activity, not only will an individual application of antimicrobial agent occur, but a synergistic effect can be initiated.

4 Claims, 15 Drawing Sheets

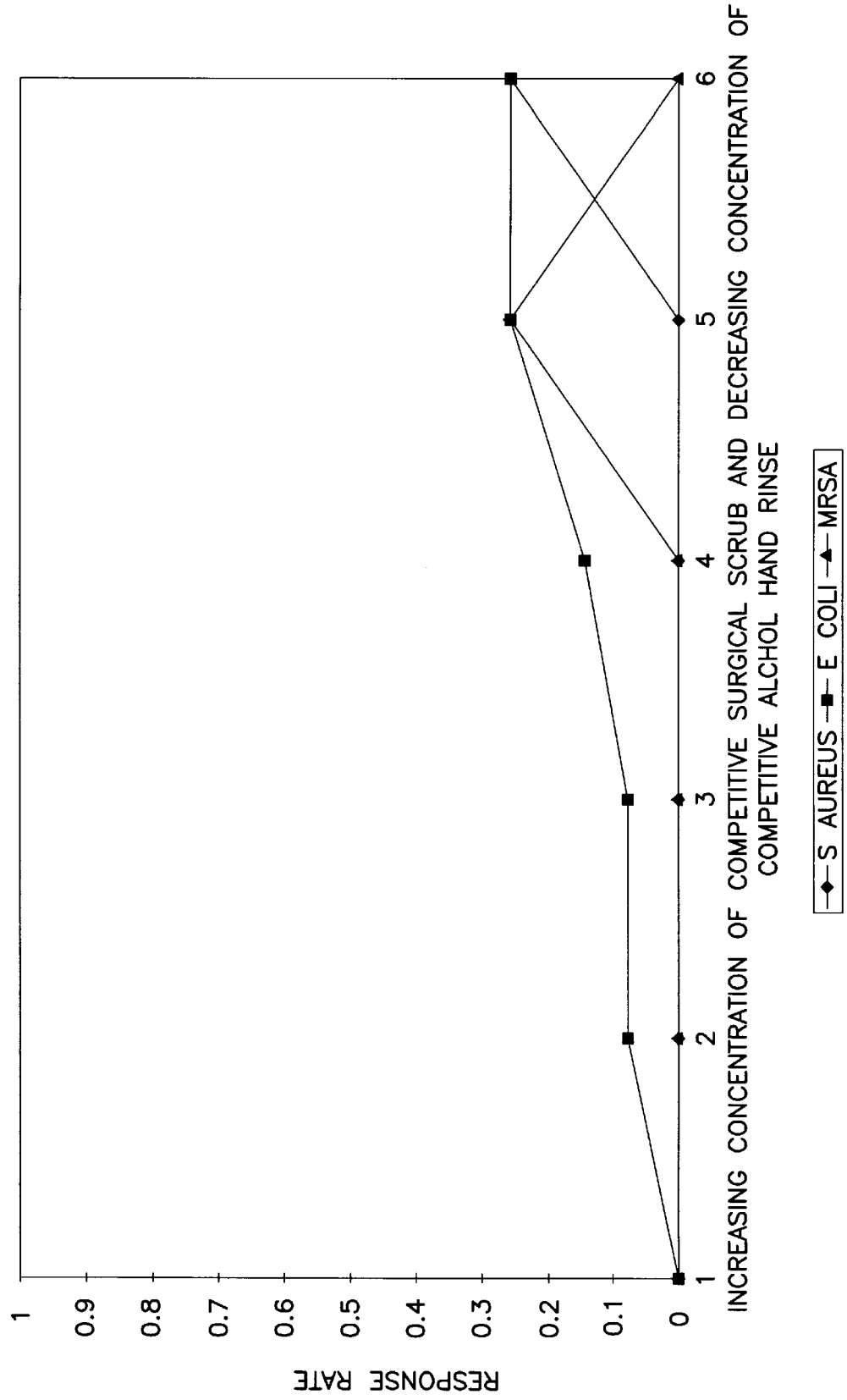

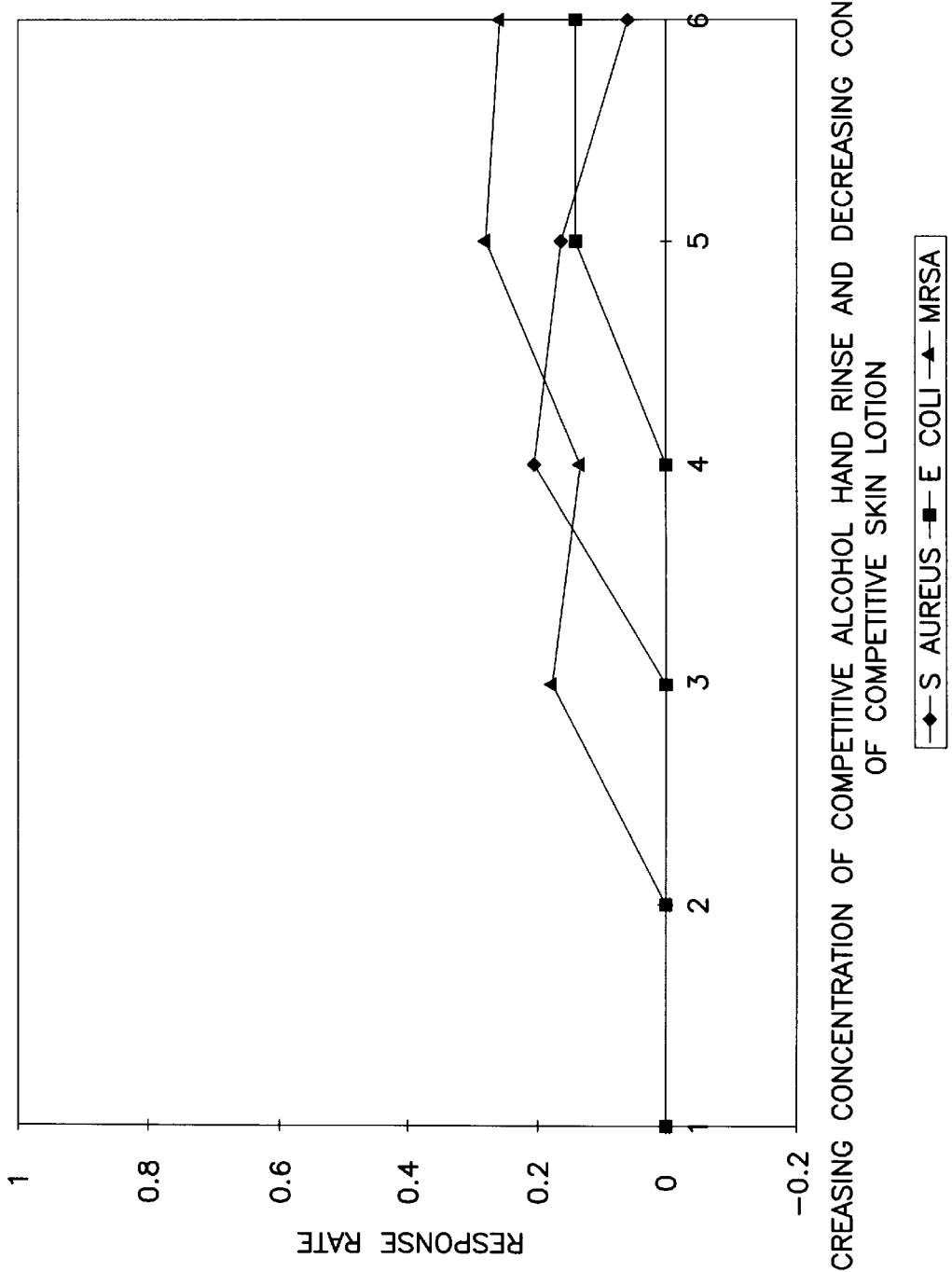

SYNERGISTIC ANTIMICROBIAL SKIN WASHING COMPOSITIONS

BACKGROUND

1. Field of the Invention

The present invention relates to the field of skin washing compositions, particularly hand washing solutions which provide an antimicrobial activity, and more particularly to combinations of solutions which may be used to provide a synergistic activity against certain microbial growth on a washed surface.

2. Background of the Art

Harmful microbial agents are easily carried by animals and people on their skin and integumatory system (e.g., hair). As people and animals contact objects and other animals and people, there is often a transfer or exchange of microbial agents. This type of event is a risk that is well appreciated in everyday life. However, in certain social environments, such as within the health care industry and the food manufacture and service industries, these types of interactions can have much more serious consequences than the casual contacts of everyday life. For example, food servers and food manufacturers are capable of exposing very large numbers of people and animals to a range of potentially dangerous microorganisms. Health care workers may come into contact with large numbers of people, come into contact with extremely infectious agents, and come into contact with extremely vulnerable people (e.g., people whose immune systems have been compromised). Similarly veterinary staff may easily transmit diseases among their patients.

Health care workers are acutely aware of the need for maintaining a sanitary environment and for maintaining the highest levels of personal hygiene, but it is difficult to actually effect a stringent policy of hygiene between contacts with patients, especially in non-surgical procedures such as in the wards and emergency rooms where there are definite constraints on time. The use of throwaway or single use coverings (such as gloves for the hands, stockings for the feet, and masks for the face) help in this regard, but there is often the potential for transmittal of microorganisms picked-up before application or after removal of the coverings.

Antimicrobial (antibacterial) soaps, lotions and creams for providing persistent activity to the person washing themselves have become fairly commonplace in the past decade. Even after washing and rinsing, some residue of the antibacterial agent remains on the skin, inhibiting the growth of organisms on the washed surfaces. There have been recent reports that the low level of antimicrobial protection provided by washes to hard surfaces may even be detrimental to overall health care protection, with the weak antimicrobial activity tending to allow strains of bacteria on the washed surfaces to develop increased resistance to the antimicrobial agents.

In health care settings, employees are now provided with a variety of hand care products throughout the various shifts in activity and throughout various locations within the health care location. These types of individual care products include general purpose handwash products in the lavatory and sink areas, health care personnel handwash products, waterless hand-rinse products, lotion products in patient contact areas, and surgical scrub products in critical care areas and surgical areas within the health care facility. The products each serve an intended purpose and have features, properties and benefits designed to meet particular needs of specific situations, such as antimicrobial activity, cleansing, moisturizing, etc. When hands are washed dozens of times daily or on each shift, many products have been found to interact with certain other products used regularly in combination or in sequence. In some cases the different products have been found to be chemically incompatible, and the features intended to be provided by one product are negated or prevented by the interaction with another product used in sequence or at a different time.

Synergy has been reported in certain unique combinations of antimicrobial agents when used in particular environments. Synergy in the field of antimicrobial agents is defined as an effect from the combined or sequential use of at least two different agents which produces an effect of greater antimicrobial activity than either of the individual agents used alone. Antagonism between at least two antimicrobial agents is defined as an antimicrobial effect from using at least two antimicrobial agents which produces a lesser antimicrobial effect than either of the at least two individual products. An antimicrobial effect which is often measured in determining synergy is the kill level or reduction in growth rate. Synergy, as noted generally above, has been reported in the antimicrobial art.

U.S. Pat. No. 5,124,355 describes a synergistic microbiocidal composition for use against microorganisms in aqueous systems, such as cooling water systems, air washer systems, and pulp and paper mill systems. The combination comprises a mixture of 2-(dicylthio)ethaneamine and 1,2-dibromo-2,4-dicyanobutane in a range of weight ratios.

U.S. Pat. No. 5,741,757 describes a biocidal mixture of materials for use in various fields such as paints, cutting oils, adhesives, weedkillers, insecticides, and the like. A single active composition is provided which comprises a mixture of a water-soluble tetrakis (hydroxymethyl) phosphonium salt and at least one surfactant selected from anionic, non-ionic and amphoteric surfactants in a range of ratios with the salt.

U.S. Pat. No. 5,611,938 describes biocidal blends of quaternary ammonium compounds and chlorine dioxide. The mixture is added to aqueous systems to control bacteria. The aqueous systems include, for example cooling water systems, air washer systems, and pulp and paper mill systems, where the presence of such bacteria can foul, plug or corrode the system.

U.S. Pat. No. 5,614,538 describes an antimicrobial composition containing pyrithione and alcohol for use against gram-negative bacteria. The mixture imparts antimicrobial activity to a composition comprising water or an organic solvent, including soap, shampoo or skin care medicament, as well as metal-working fluids.

U.S. Pat. No. 5,374,536 describes a product detection test for biocides, and identifies a number of specific combinations within single solutions which pass the test. The materials are generally described for particular use with aqueous waters or water systems, and identifies many different specific fields within that class, particularly paper stock, paper finish, pulp and paper manufacture, textile processing waters, food processing waters, cooling waters, recirculation waters, effluent streams, fermentation streams, and the like. Specific biocides are listed within the patent.

U.S. Pat. No. 5,776,960 describes antimicrobial compositions containing an ionene polymer and a pyrithione salt, and methods of using the composition. The compositions are particularly described for use in preserving or controlling the growth of at least one microorganism in various types of industrial media or materials, such as, but not limited to, dyes, pastes, pulps, lumber, leathers, textiles, wood chips, tanning liquor, paper mill liquor, polymer emulsions, paints, papers, coating and sizing agents, metalworking fluids, geological drilling lubricants, petrochemicals, cooling water systems, recreational water, influent plant water, waste water, pasteurizers, retort cookers, pharmaceutical formulations, cosmetic and toiletry formulations, and the like.

U.S. Pat. No. 5,736,574 describes pharmaceutical/cosmetic composition comprising an antimicrobial admixture. The admixture comprises at least one antimicrobial hydrolipid and/or lipid, and as an antimicrobially synergistic amount of at least one glyceryl monoalkyl ether.

U.S. Pat. No. 5,569,461 describes a topical antimicrobial composition and method of use. The composition is described as useful for the disinfecting, cleansing, treating and conditioning of skin, and comprises a propylene glycol monoester of capric or caprylic acid, a second propylene glycol monoester of capric or caprylic acid, a synergist (e.g., acidic chelating agents and food grade phenols), propylene glycol, a surfactant and a vehicle.

Additional antimicrobial systems are still desirable, particularly where those systems may have additional flexibility in use.

SUMMARY OF THE INVENTION

The present invention describes a synergistic composition and a synergistic system for use in treating the skin and hair of people and animals. The system comprises separate treatment compositions (solution, dispersions, emulsions, suspensions or other liquid or liquefiable materials), one treatment with a composition comprising at least 0.1% by weight of the generic class of antimicrobial agents inclusive of Triclosan (the name Triclosan, as used in the specification and claims, but not the Examples, is intended to be generic to the chemical class inclusive of the compound known as Triclosan, unless other wise stated) and another composition being selected from the group consisting of:

a) a washing solution comprising chlorhexidine gluconate;

b) a washing solution comprising Triclosan, preferably in a different weight percentage of Triclosan than said one composition, comprising an amount at least greater than 0.3% Triclosan;

c) a washing solution comprising an alcohol (e.g., ethanol, isopropanol).

These compositions do not have to be applied in any particular order, and more than two compositions may be combined in separate or sequential applications.

The single compositions of the present invention comprise a single composition comprising at least 0.1% by weight Triclosan and at least one synergistic additive selected from the group consisting of chlorhexidene gluconate, a solution containing greater than 0.3% Triclosan and an alcohol. These compositions, both as single compositions or as separate compositions have been found to provide synergistic antimicrobial effects. It is surprising that even when the separate compositions are applied with significant periods of time between application of the individual compositions (e.g., 2, 3, 5 or even 8 hours between applications) a synergistic effect may be provided. This is believed to be at least in part because some of the materials may persist on the skin and later would be combined with the application of the other synergistic composition.

Because of the unique ability to provide synergy in separate compositions, with gaps in time between application of the separate materials, a system of washing, cleansing, lubricating, and moisturizing compositions may be provided within a health care complex. In this manner, as an individual applies the various compositions over the course of the day, due to varying activity, not only will an individual application of antimicrobial agent occur, but a synergistic effect can be initiated.

BRIEF DESCRIPTION OF THE FIGURES

FIG. 14 is a graph showing synergy evaluation between a commercially available surgical scrub and commercially available alcohol hand rinse.

FIG. 15 is a graph showing a non-synergistic effect between a commercially availabe alcohol hand rinse and commmercially available skin lotion.

DETAILED DESCRIPTION OF THE INVENTION

Figure 1:
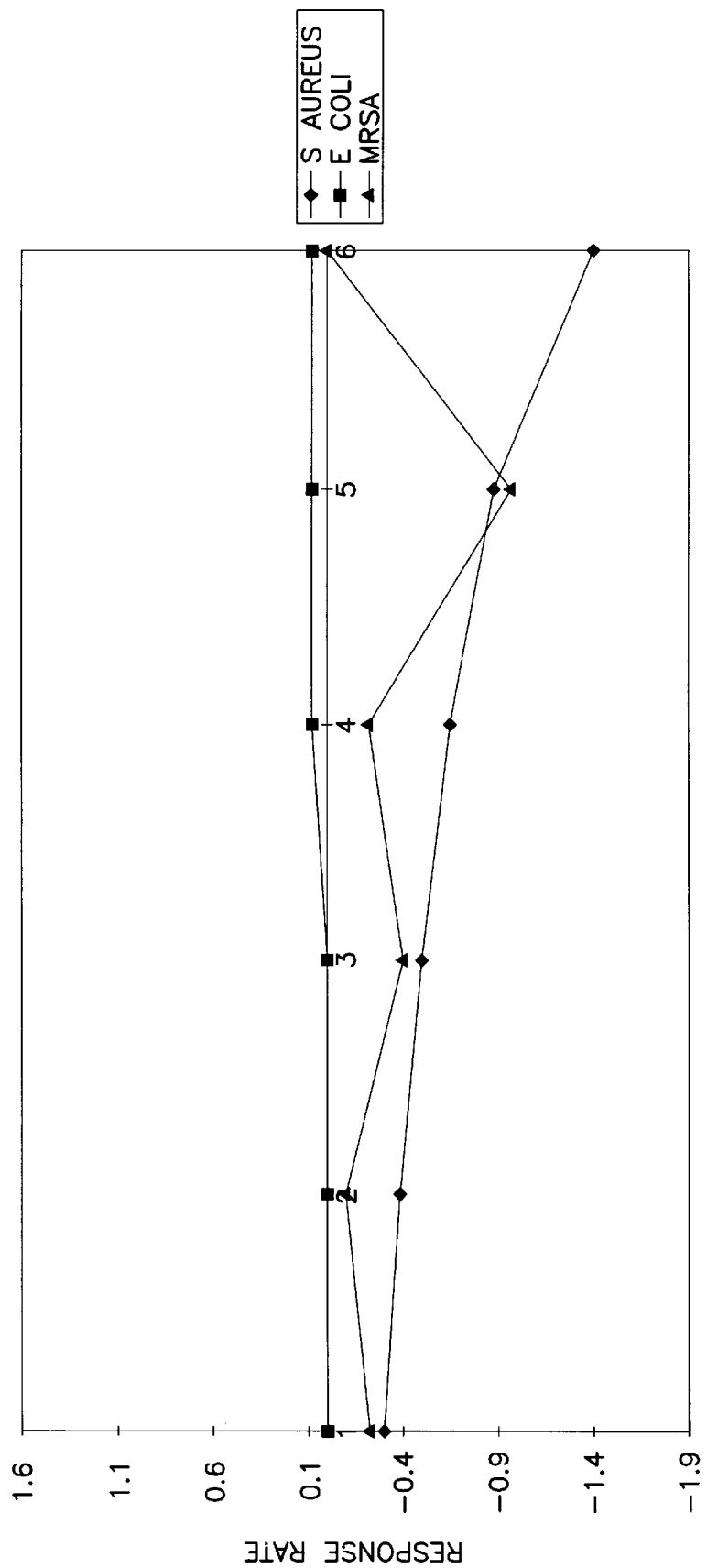
FIG. 1 is a graph showing synergy between a general purpose handwash and health care personnel handwash.
Figure 2:
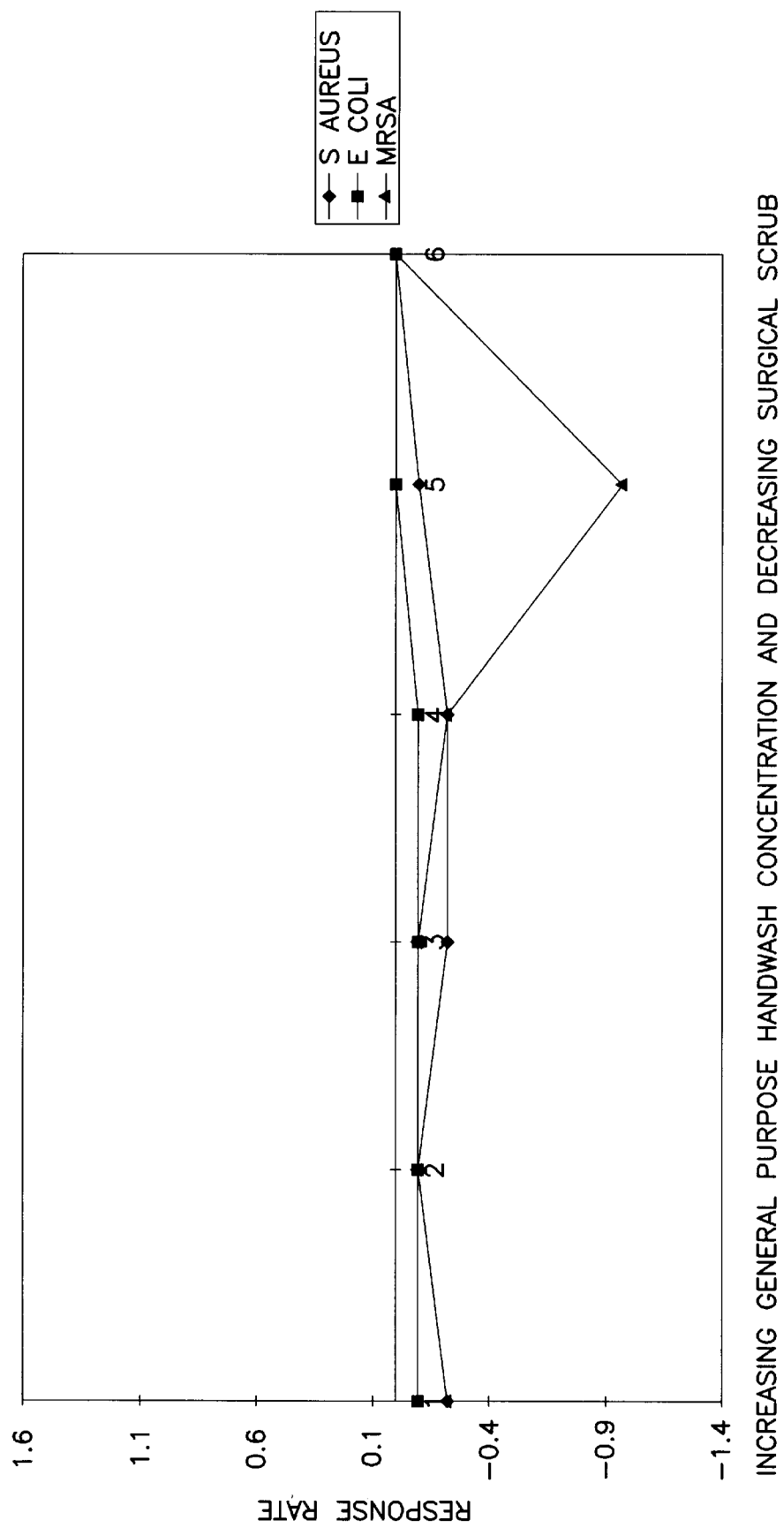
FIG. 2 is a graph showing synergy evaluation between a general purpose hand wash and a surgical scrub.
Figure 3:
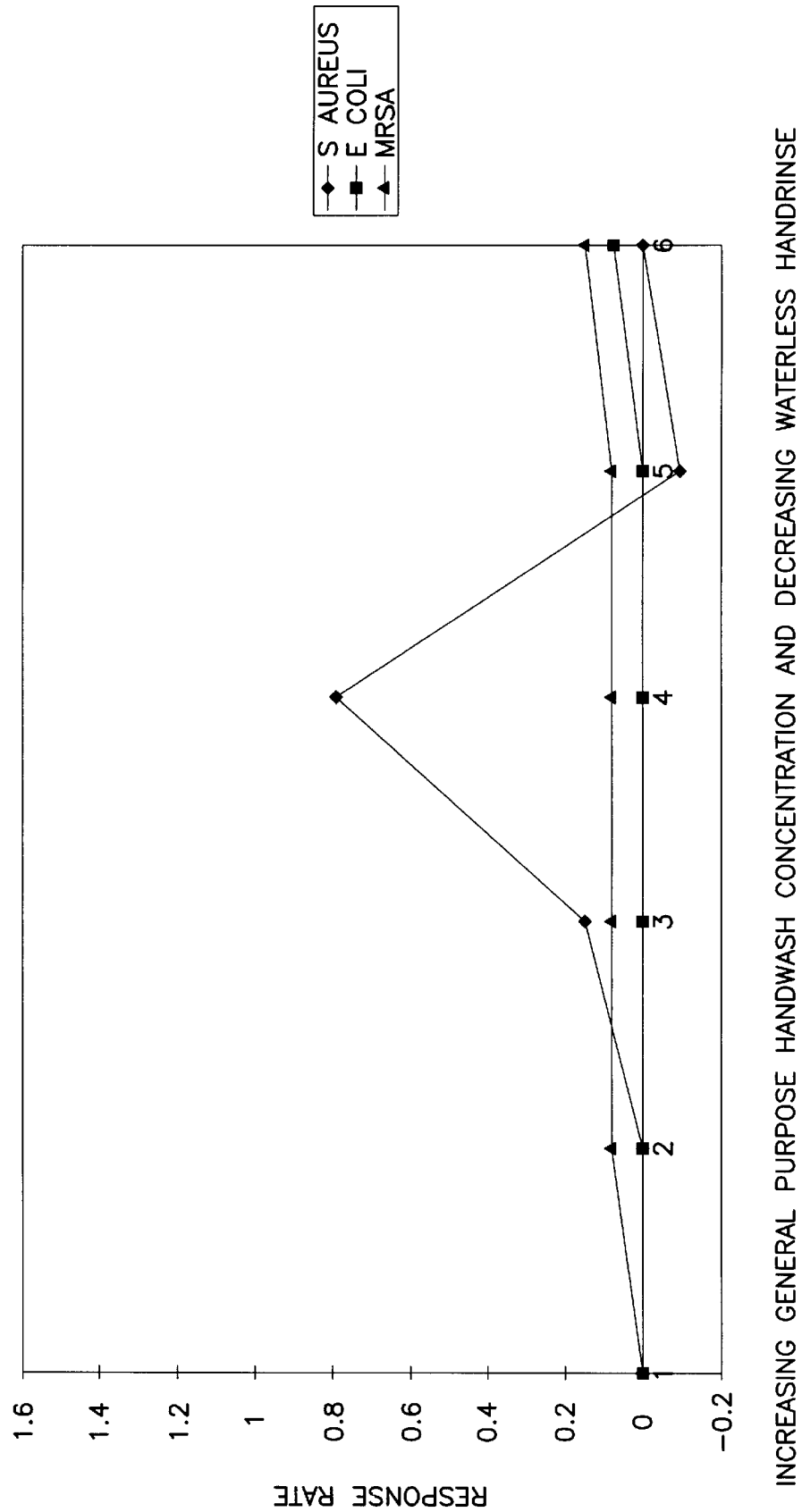
FIG. 3 is a graph showing synergy evaluation between a general purpose hand wash and a waterless handrinse.
Figure 4:
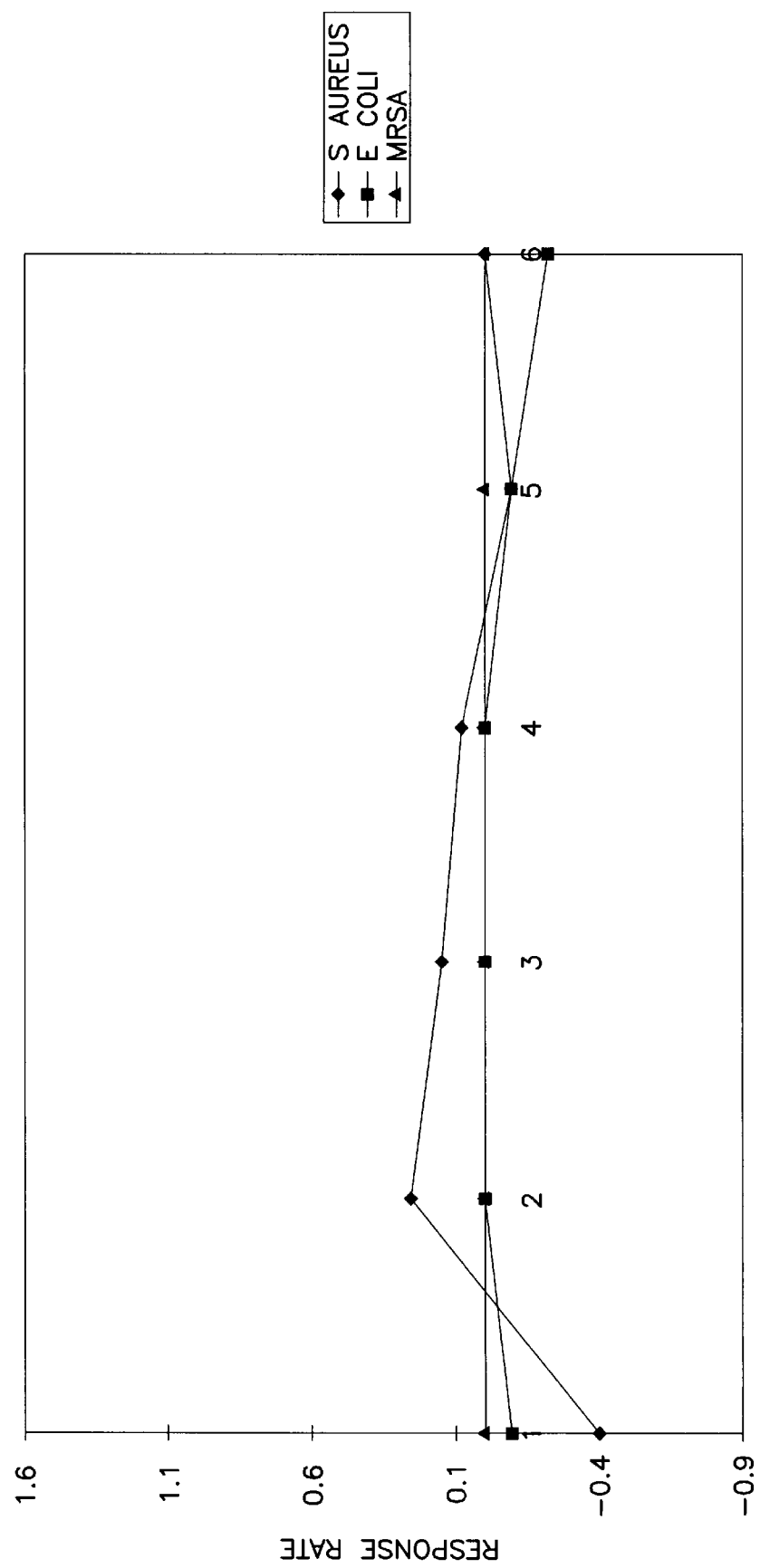
FIG. 4 is a graph showing synergy evaluation between a general purpose handwash plus a hand lotion.
Figure 5:
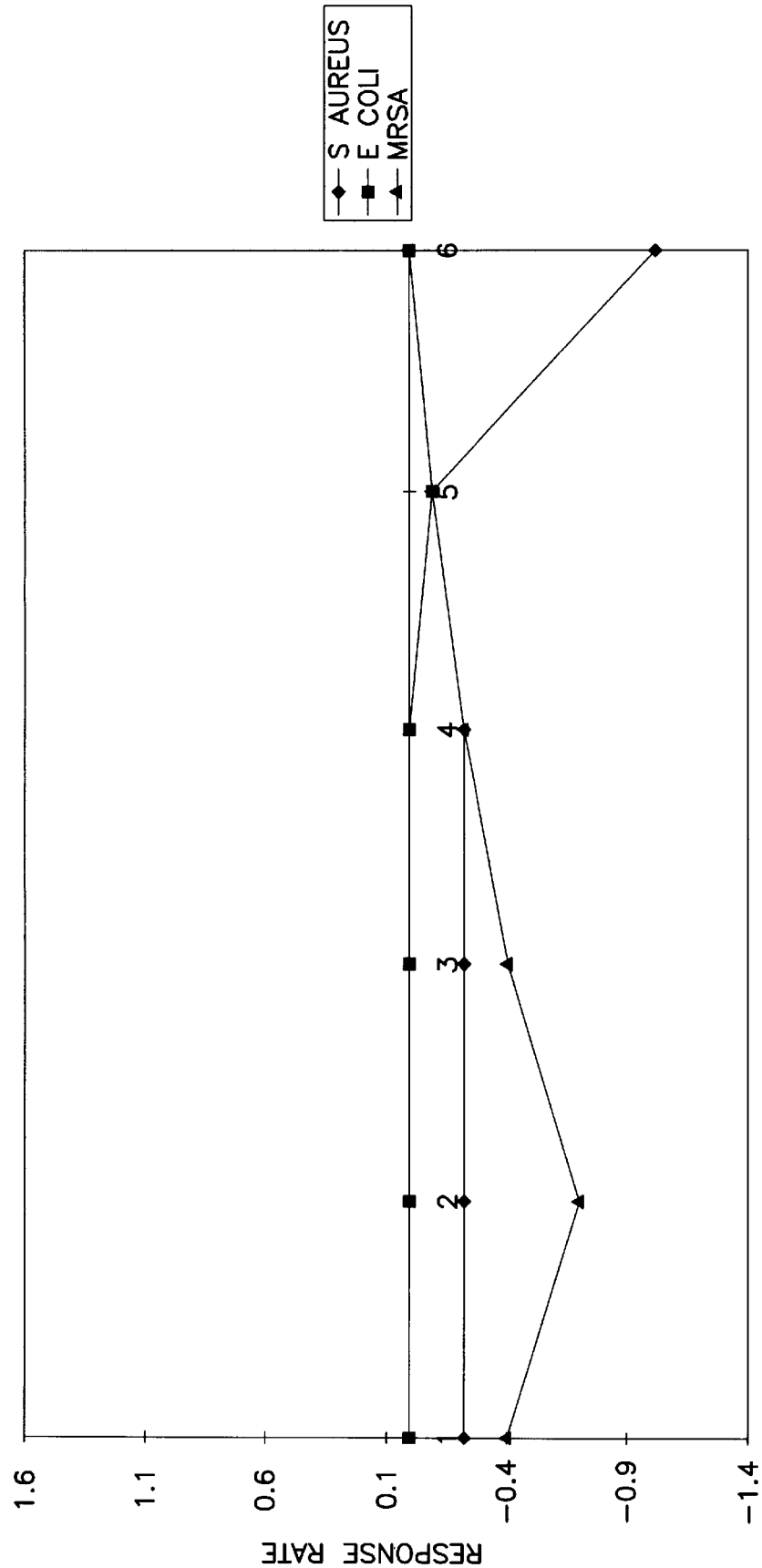
FIG. 5 is a graph showing synergy evaluation between a health care personnel handwash and a surgical scrub.
Figure 6:
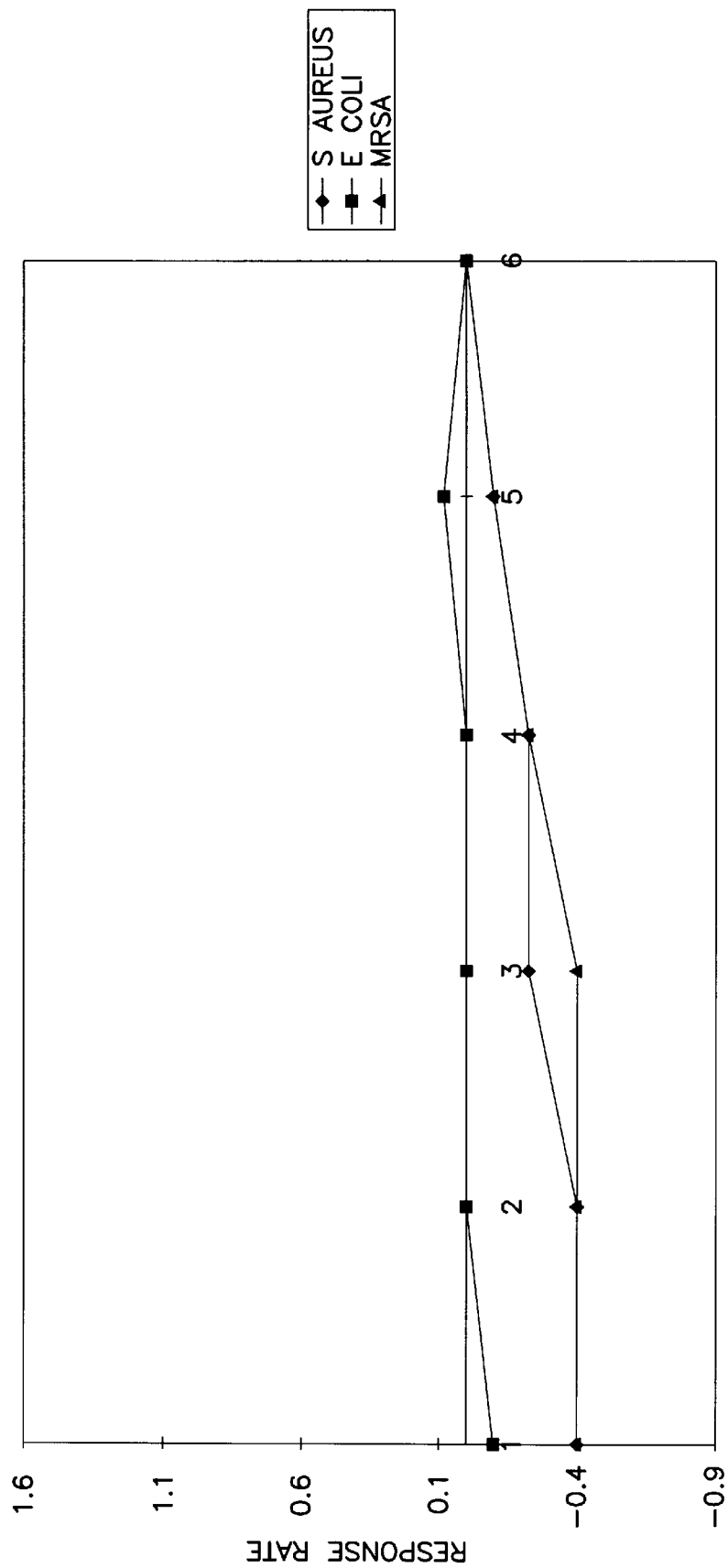
FIG. 6 is a graph showing synergy evaluation between a health care personnel handwash and a waterless handrinse.
Figure 7:
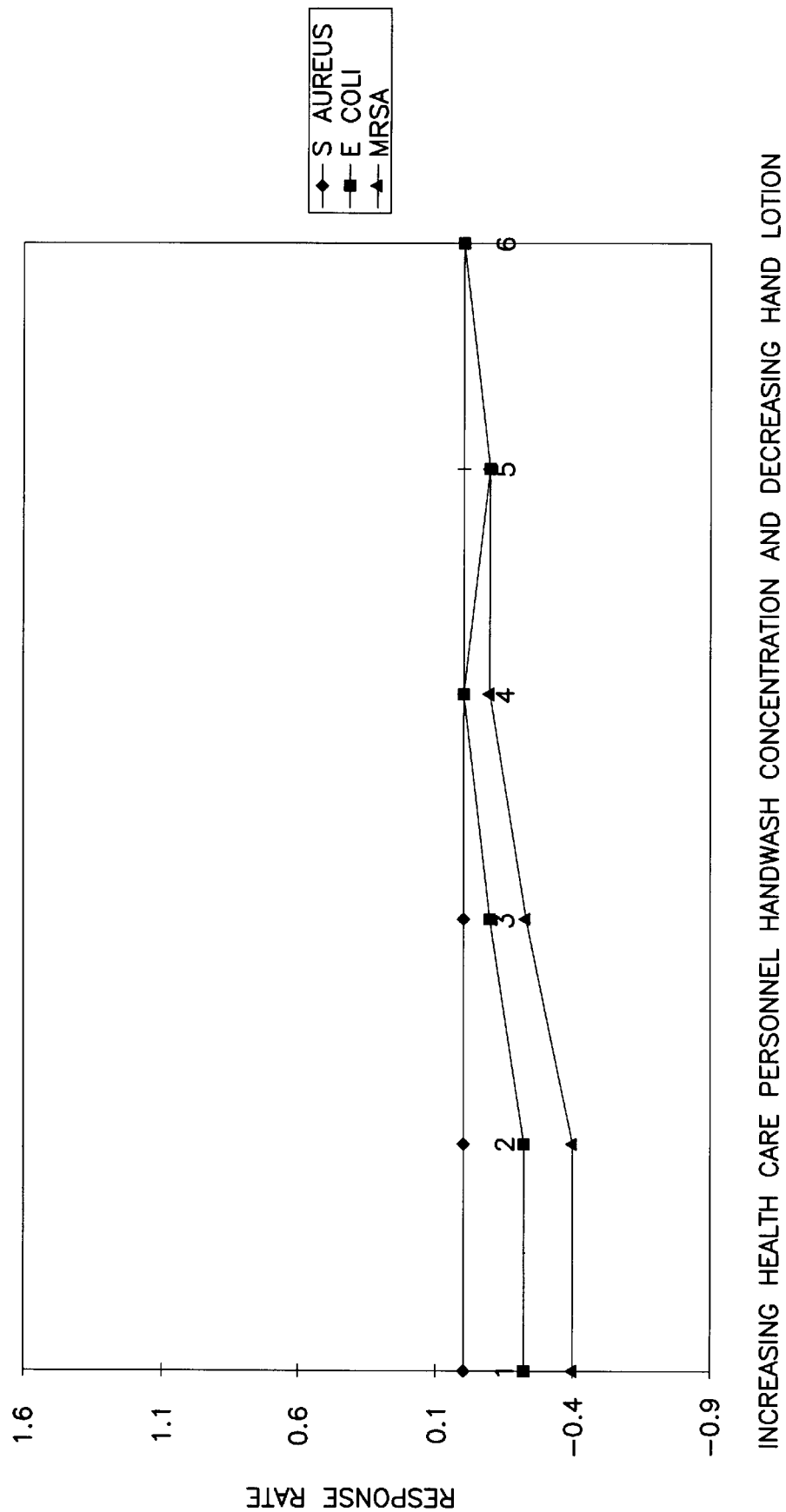
FIG. 7 is a graph showing synergy evaluation between a healthcare personnel handwash and a hand lotion.
Figure 8:
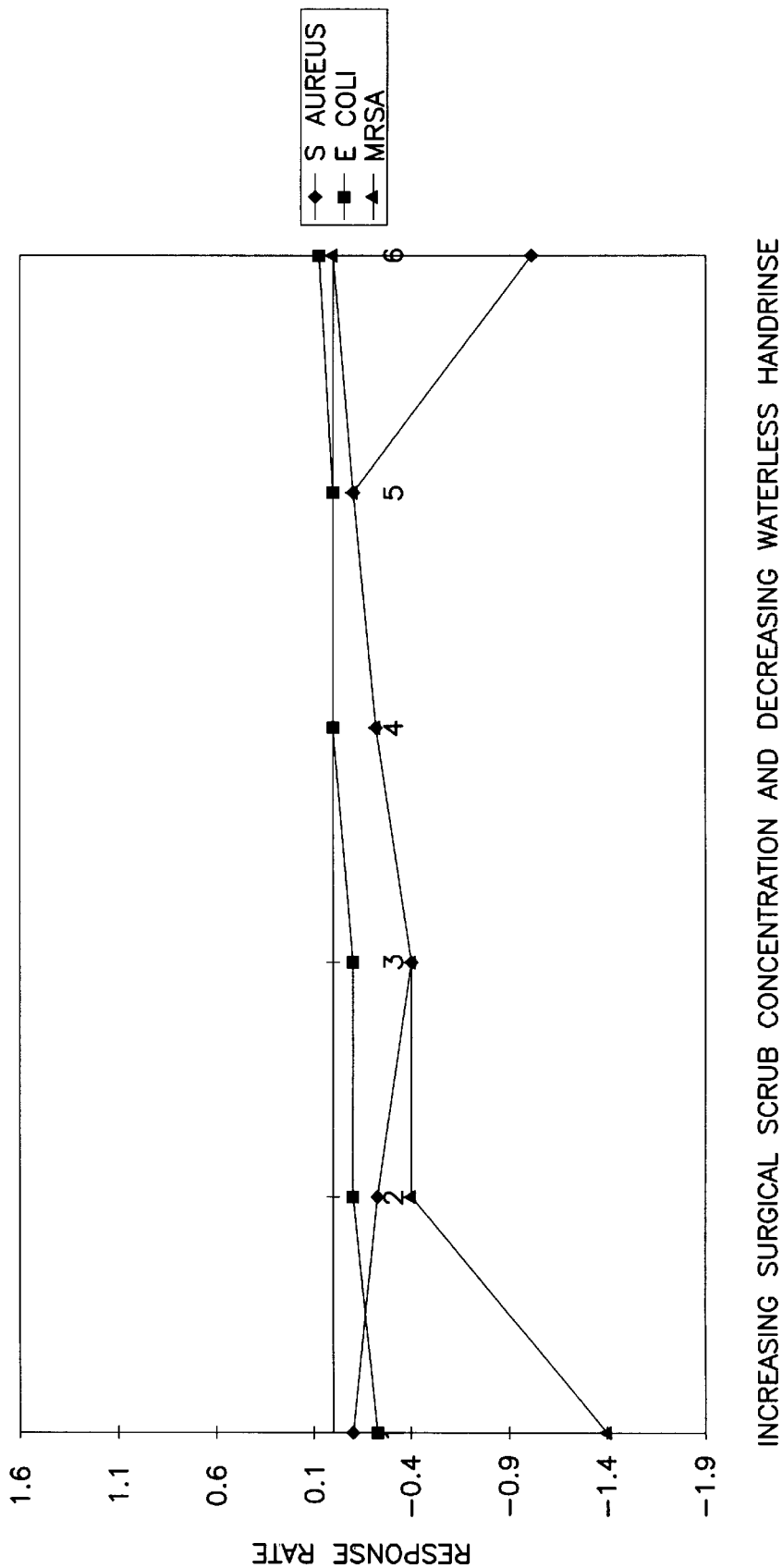
FIG. 8 is a graph showing synergy evaluation between surgical scrub and a wateerless handrinse.
Figure 9:
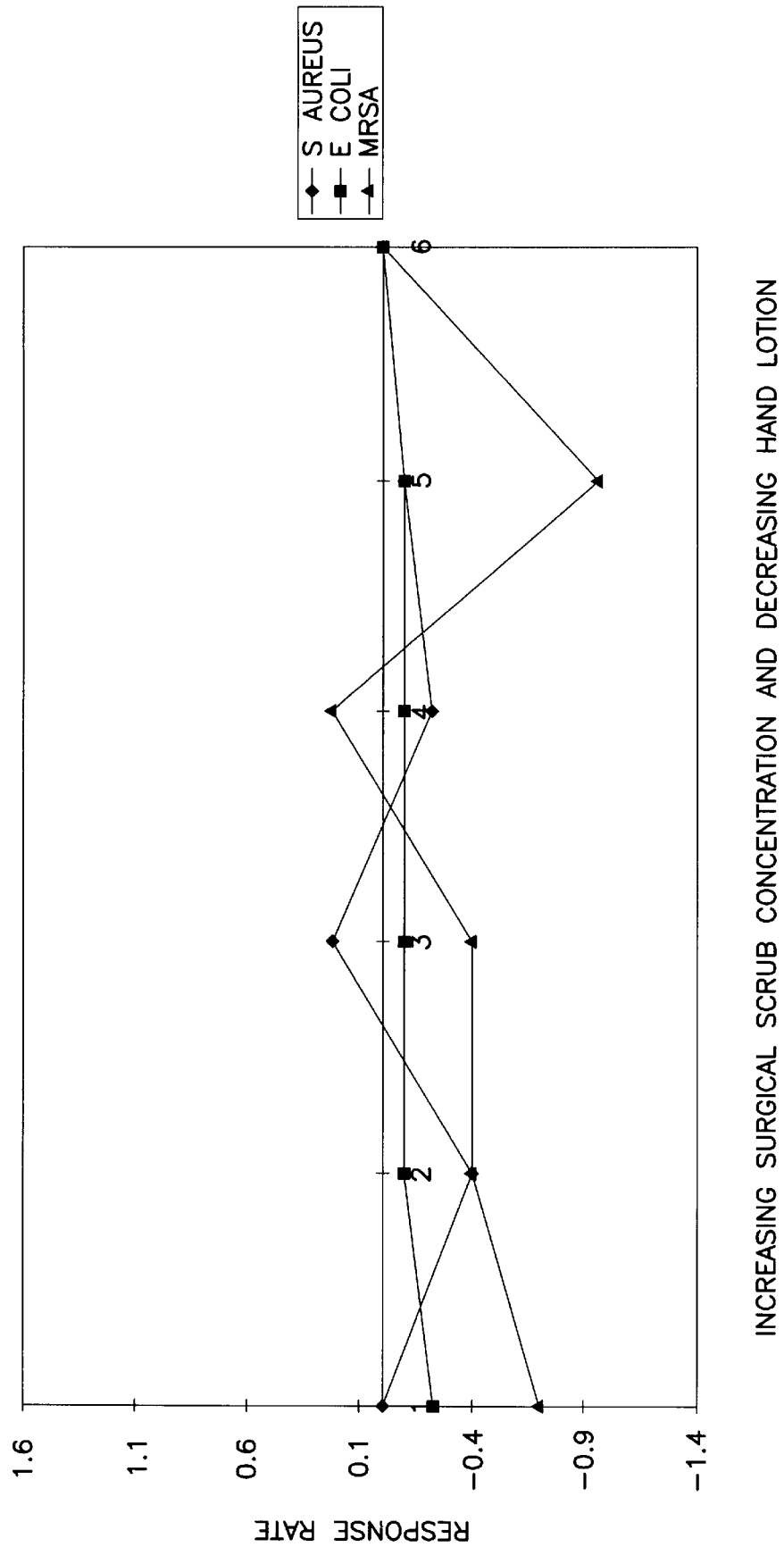
FIG. 9 is a graph showing synergy evaluation between a surgical scrub and a hand lotion.
Figure 10:
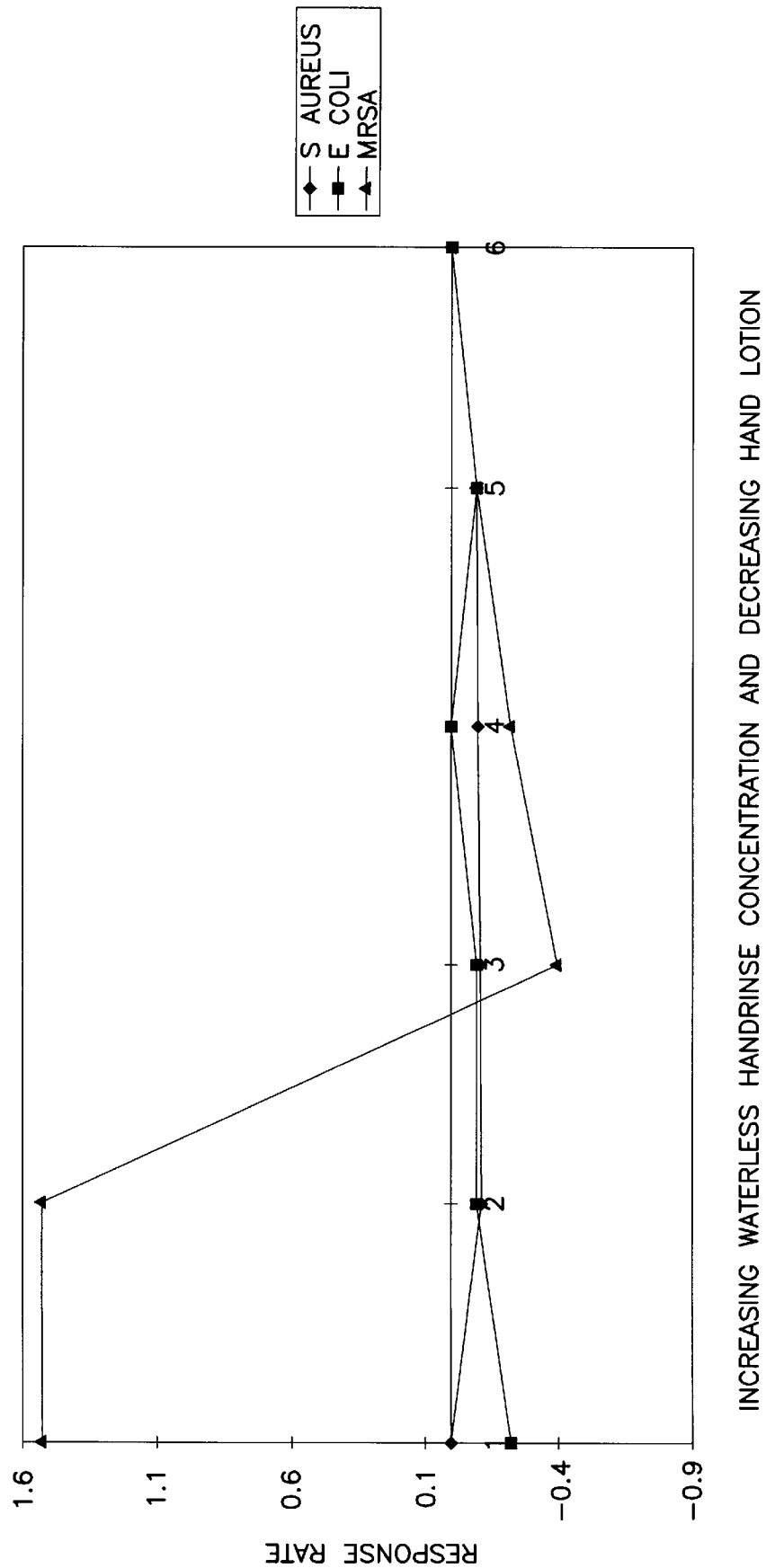
FIG. 10 is a graph showing Skin Synergy of a Waterless Hand Rinse Plus Hand Lotion.
Figure 11:
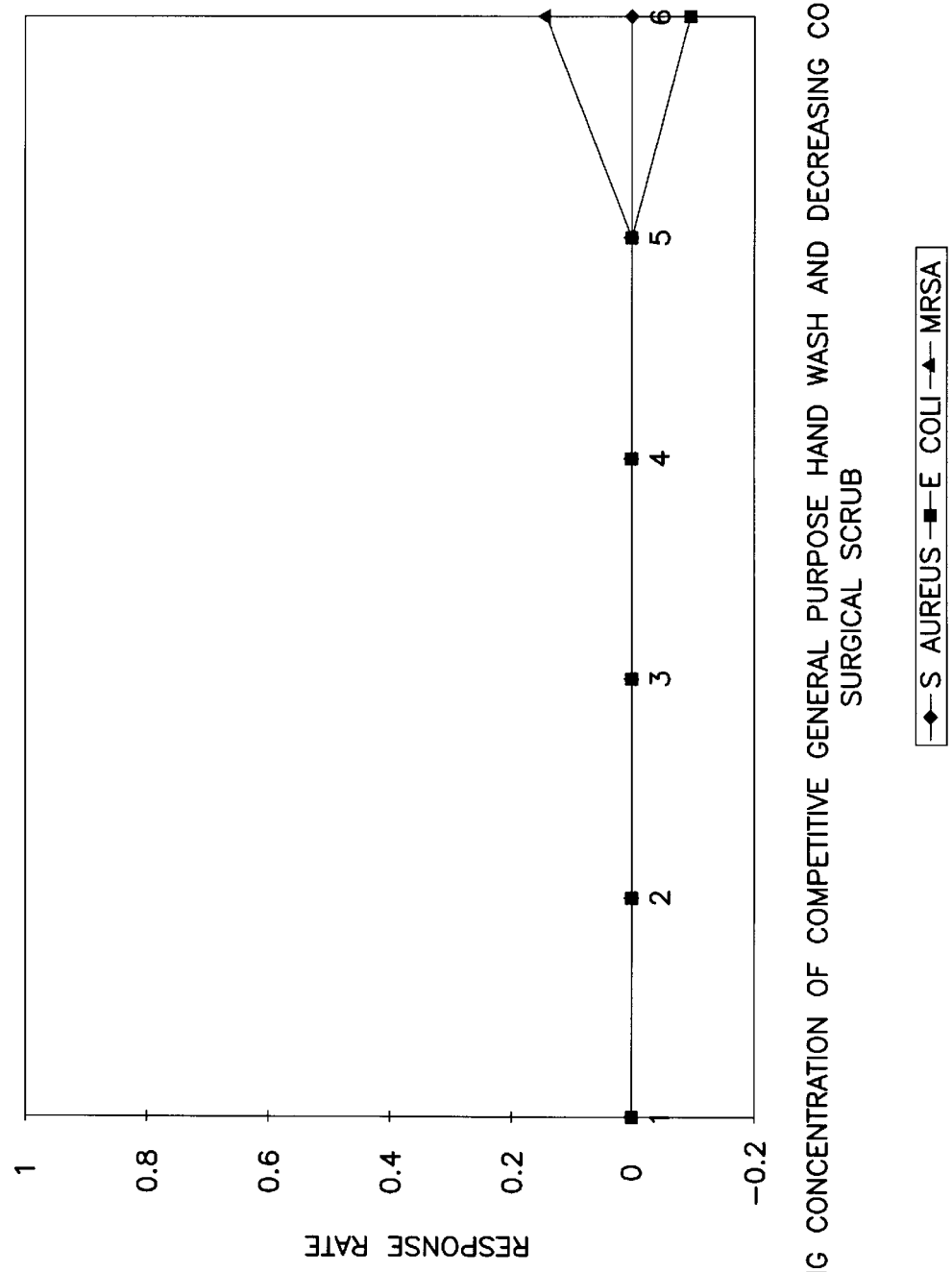
FIG. 11 is a graph showing synergy evaluation between a commercially available antimicrobial general purpose handwash and commercially available surgical scrub
Figure 12:
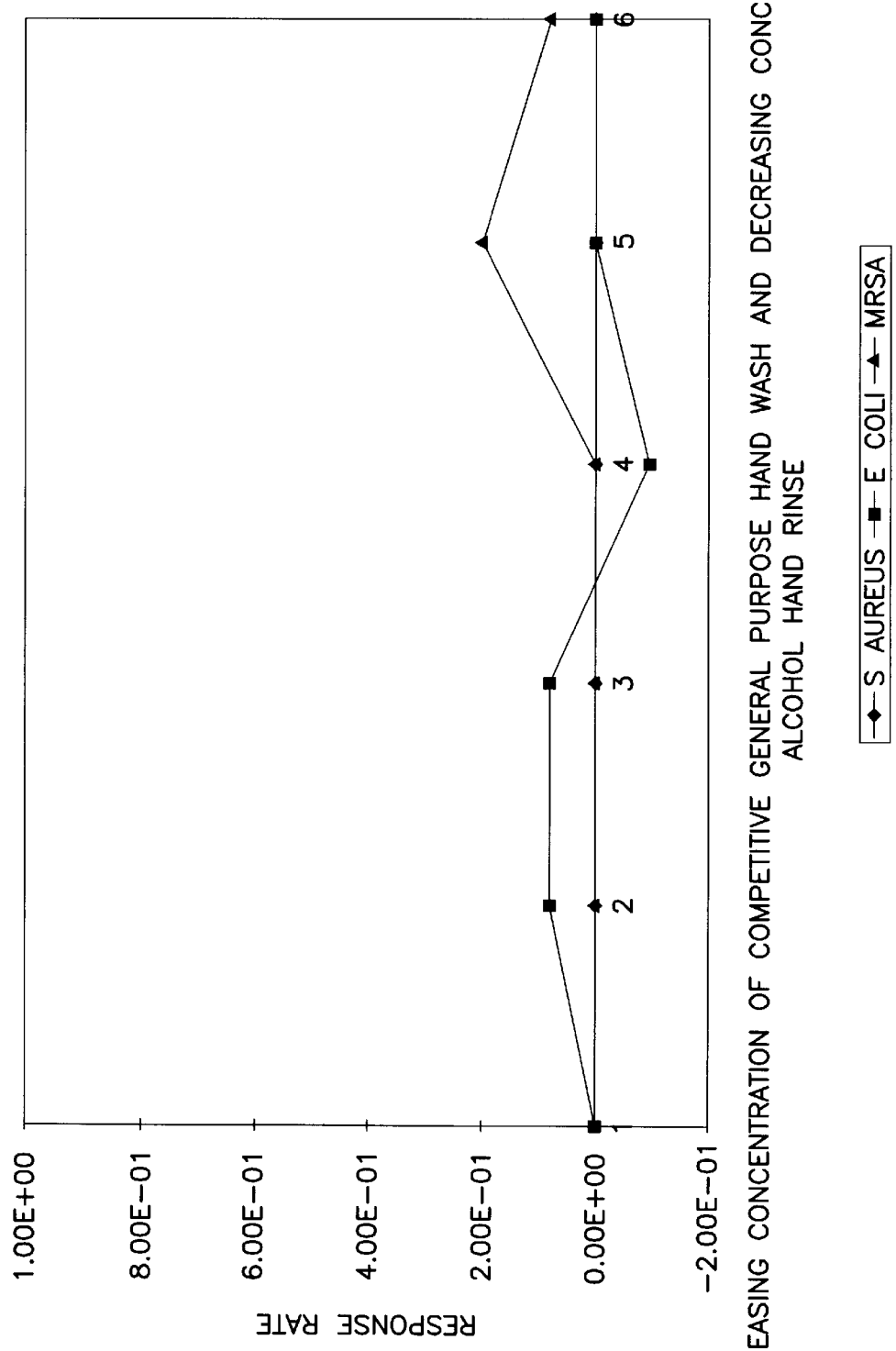
FIG. 12 is a graph showing synergy evaluation between a commercially available antimicrobial general purpose handwash and commercially available alcohol hand rinse.
Figure 13:
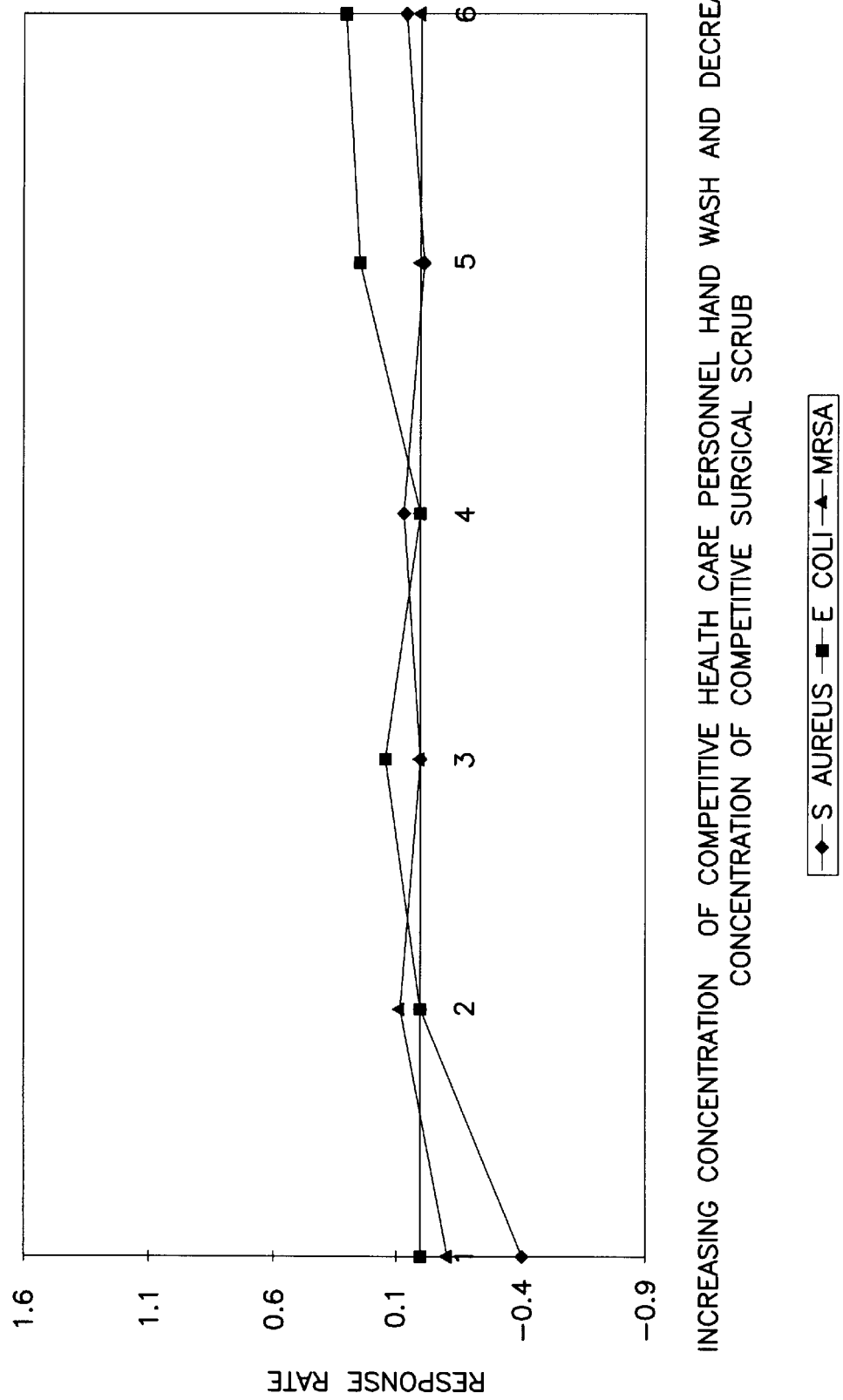
FIG. 13 is a graph showing synergy evaluation between a commercially available healthcare personnel hand was and commercially available surgical scrub.

In various fields, the term 'synergy' has specific and defined meanings. Within the practice of the present invention, in the field of antimicrobial activity, the term specifically refers to the fact that in the calculation of values and their display in graphs as shown in the Figures briefly described above, synergy is displayed and defined by a negative number on the graph, neutrality is shown by a value of zero, and antagonistic behavior is shown by a positive number on the graph. This definition is consistent with traditional practice within the field. In the graphic representations, each point on the graph represents varying concentrations of two combined compositions, as later described in the Examples and data in greater detail.

The present invention relates to single use compositions and sequential use compositions for treatment of skin and/or hair which provide synergistic antimicrobial effects. The sequential compositions may be used in any sequence of the at least two separate compositions, and synergistic antimicrobial effects will be provided. The individual compositions may be provided, for example, as soaps, scrub solutions, moisturizers, lubricating solutions (as for easing the application of gloves on a hand), cleansing solutions, sterilization applications, presurgical washes, multiple wash sets, and any other skin treatment which may be applicable to the health care, veterinary care, or food manufacture/food service industries. Kits may also be provided wherein at least two different synergistically interactive compositions may be provided at a single application station (lavatory, scrub room, shower or bath stall, room entry, room exit, ER room, admission room, treatment room, X-ray room, kitchen, and the like), or the different and separate compositions may be spread around the various different application stations. The compositions may be provided as a kit, with the various different synergistic compositions provided within a single package. As the Triclosan is used in synergistic combination with each of the other compositions (including a Triclosan composition with higher concentrations, e.g., greater than 0.3%), the kit might be provided with proportionation among the various compositions, such as the Triclosan composition being provided in the kit in an amount of at least 1.5 times the amount of any other single composition. More than two compositions may be provided in each kit, with different antimicrobial compositions and ingredients provided in the various products. For example, one general application liquid soap may have the at least 0.1% Triclosan, a moisturizer may have the chlorhexidine gluconate, a scrub solution may have the alcohol, a post operation treatment may have greater than 0.3% (e.g., at least 0.35%, at least 0.4%, or at least 0.5%) Triclosan, and the like. Individual soaps may be provided with each of the ingredients, with recommendations as to sequence (although not required for synergistic performance, it might well be desirable to have the alcohol containing composition applied before the moisturizing composition as a matter of common sense).

The invention may also be practiced therefore by providing a washing station having at least two washing compositions available for use, said at least two washing compositions being selected from the group consisting of:
 a) one washing solution comprising Triclosan and another washing solution comprising chlorhexidine gluconate;
 b) two washing solutions comprising at least 0.1% Triclosan and at least one of said two washing solutions comprising greater than 0.3% Triclosan; and
 c) one washing solution comprising Triclosan and another washing solution comprising an alcohol (e.g., ethanol, isopropanol);
or more generally a washing station having at least two washing compositions available for use, one washing solution comprising at least 0.1% by weight of Triclosan and another washing solution being selected from the group consisting of:
 a) a washing solution comprising chlorhexidine gluconate;
 b) a washing comprising Triclosan comprising greater than 0.3% Triclosan; and
 c) a washing solution comprising an alcohol (e.g., ethanol, isopropanol).

The method is for washing a skin or hair surface (particularly of a live person or animal) to reduce the growth of microbial agents thereon, said method comprising washing said surface with at least two solutions in the order of a first wash solution and then a second wash solution, said first and second wash solutions selected from the group consisting of:
 a) one washing solution comprising Triclosan and another washing solution comprising chlorhexidine gluconate;
 b) two washing solutions comprising at least 0.1% Triclosan and at least one of said two washing solutions comprising greater than 0.3% Triclosan; and
 c) one washing solution comprising Triclosan and another washing solution comprising an alcohol (e.g., ethanol, isopropanol);
or more generally a method using at least two washing compositions available for use, one washing solution comprising at least 0.1% by weight of Triclosan and another washing solution being selected from the group consisting of:
 a) a washing solution comprising chlorhexidine gluconate;
 b) a washing comprising Triclosan comprising greater than 0.3% Triclosan;
 c) a washing solution comprising an alcohol (e.g., ethanol, isopropanol).

It is important to note that, unless otherwise specifically identified, the naming of a composition as the first or second or third does not limit the order in which they are applied. As noted elsewhere, the various synergistic materials may be applied in any order, whether the individual compositions are numbered first, second, third, fourth or fifth. The composition may be mixed into a single composition to be applied (either by compounding by the manufacturer or by mixing in a dispenser on site). The terminology that a composition is liquifiable is intended to include bar soaps, dissolvable pellets or slugs, powders, or other materials that would have to be mixed with a liquid (such as tap water) to become liquid for application to the skin or hair as a treatment according to the present invention. These and other aspects of the invention will be further described in the following, non-limiting examples.

In the following examples, the following commercial Trade Name materials are used:

| PRODUCT NAME | PRODUCT CLASS | ACTIVE INGREDIENT % | CHEMICAL ACTIVE | CHEMICAL EQUIVALENT | CHEMICAL CLASS |
|---|---|---|---|---|---|
| ENDURE 100 | GEN. PURP. HAND WASH | Triclosan 0.2% | Triclosan | p-chloroxylenol Triclosan, and Triclocarban | Aliphatic phenol derivatives |
| BACTI-STAT PLUS | HEALTH CARE PERS. HAND WASH | Triclosan 1.0% | Triclosan | p-chloroxylenol Triclosan, and Triclocarban | Aliphatic phenol derivatives |

-continued

| PRODUCT NAME | PRODUCT CLASS | ACTIVE INGREDIENT % | CHEMICAL ACTIVE | CHEMICAL EQUIVALENT | CHEMICAL CLASS |
|---|---|---|---|---|---|
| SCRUB STAT | SURGICAL SCRUB | Chlorhexidine Gluconate 4% | Chlorhexidine Gluconate | Chlorhexidine salts, and other carboxylic acid esters | Antimicrobially active cationic species |
| CIDA-RINSE GEL | ALCOHOL RINSE | Ethanol 70% | Ethanol | isopropanol, methanol | C1–C4 alcohols |
| ENDURE 500 | LOTION | Triclosan 0.3% | Triclosan | p-chloroxylenol Triclosan, and Triclocarban | Aliphatic phenol derivatives |

The various classes of antimicrobial compounds such as aliphatic phenol derivatives, antimicrobially active cationic species, alcohols (e.g., methanol, ethanol, propoanol, butanol, isopropanol, isobutanol, etc.), and the like are compounds well understood in the art and well recognized as a class within the art.

EXAMPLES

The following non-limiting examples provide assistance in enabling one of ordinary skill in the art to make and use the invention and describe what the inventors believe is the best mode of practicing the invention. The Examples are intended to be instructive and not limiting, being exemplary and not limiting in the use of materials, times, conditions and other parameters used within the Examples.

The objective of the examples was to determine the minimum inhibitory concentration (MIC) of EPP Endure™ Hand Care Products (Endure™ 100, Bacti-Stat Plus™, Scrub Stat 4™, Cida™ Rinse Gel, and Endure™ 500), then determine any synergistic relationship between the products. Testing was conducted against *Staphylococcus aureus* ATCC 6538, *Escherichia coli* ATCC 11229 and methicillin resistant *Staphylococcus aureus* HL 121.

Test Method

The Minimum Inhibitory Concentration (MIC) Method used in the Examples is as follows:

1. Each test substance was diluted in 10 mL of test-system-specific nutrient broth prepared at a 2× concentration to obtain an initial concentration of 1:2 test substance.
2. A series of 1:2 dilutions were made in 10 mL of nutrient broth starting with the initial concentration of 1:2 and ending with a final concentration of 1:1024 test substance.
3. A 24 hour broth culture of the test system containing ~$10^8$ CFU/mL was diluted in nutrient broth to obtain ~$10^7$ CFU/mL.
4. Each 10 mL test tube (hereinafter merely referred to as a "tube") containing the varying concentrations of the product was inoculated with 0.1 mL of the test system suspension to obtain ~$10^5$ CFU/mL of the test system in the test tube.
5. Test tubes were observed for growth after a 24-hour incubation period at the temperature appropriate for the test system.
6. The MIC is the minimum level of active ingredient necessary for the complete inhibition of growth of the test system. The MIC was recorded as the lowest concentration which no turbidity (growth) was visually detected in the tube. If all tubes in a series were turbid, and it was not possible to determine whether the turbidity was due to bacterial growth or the handsoap itself, then those tubes were subcultured to an appropriate growth medium to determine the Minimum Bactericidal Concentration (MBC). The MBC is defined as the lowest concentration that demonstrated no survivors.

An outline of the Skin Synergy Method is as follows:

1. Each test substance was diluted in 50 mL of test-system-specific nutrient broth prepared at a 2× concentration to obtain an initial concentration of 1:2 test substance.
2. A series of 1:2 dilutions were made in 50 mL of nutrient broth, starting with the initial concentration of 1:2 and ending with 2× the MIC/MBC for the specific product and organism (i.e. for an MIC of 1:16, a 1:8 dilution would be prepared).
3. Each 2× concentration was combined in sequence; outlined by the table below. The following product combinations were tested: A+B, A+C, A+D, A+E, B+C, B+D, B+E, C+D, C+E, and D+E.
   Note: Milliliter quantities were used in each of the cases listed.

| | (1st letter + 2nd letter + 2X nutrient broth) | | | | | |
|---|---|---|---|---|---|---|
| | 100% $2^{nd}$ letter | 80% 2nd letter | 60% 2nd letter | 40% 2nd letter | 20% 2nd letter | 0% 2nd letter |
| 100% 1st letter | 5 + 5 + 0 | 5 + 4 + 1 | 5 + 3 + 2 | 5 + 2 + 3 | 5 + 1 + 4 | 5 + 0 + 5 |
| 80% 1st letter | 4 + 5 + 1 | 4 + 4 + 2 | 4 + 3 + 3 | 4 + 2 + 4 | 4 + 1 + 5 | 4 + 0 + 6 |
| 60% 1st letter | 3 + 5 + 2 | 3 + 4 + 3 | 3 + 3 + 4 | 3 + 2 + 5 | 3 + 1 + 6 | 3 + 0 + 7 |
| 40% 1st letter | 2 + 5 + 3 | 2 + 4 + 4 | 2 + 3 + 5 | 2 + 2 + 6 | 2 + 1 + 7 | 2 + 0 + 8 |

-continued

| | (1st letter + 2nd letter + 2X nutrient broth) | | | | | |
|---|---|---|---|---|---|---|
| | 100% 2$^{nd}$ letter | 80% 2nd letter | 60% 2nd letter | 40% 2nd letter | 20% 2nd letter | 0% 2nd letter |
| 20% 1st letter | 1 + 5 + 4 | 1 + 4 + 5 | 1 + 3 + 6 | 1 + 2 + 7 | 1 + 1 + 8 | 1 + 0 + 9 |
| 0% 1st letter | 0 + 5 + 5 | 0 + 4 + 6 | 0 + 3 + 7 | 0 + 2 + 8 | 0 + 1 + 9 | 0 + 0 + 10 |

Note: A total of 36 tubes per combination were tested. A total of 10 mL of product combination/2X nutrient broth was present in each tube.

4. A 24-hour broth culture of the test system containing ~$10^8$ CFU/mL was diluted in nutrient broth to obtain ~$10^7$ CFU/mL.
5. Each 10 mL tube containing the varying concentrations of the product was inoculated with 0.1 mL of the test system suspension to obtain ~$10^5$ CFU/mL of the test system in the test tube.
6. Test tubes were observed for growth after a 24-hour incubation period at the temperature appropriate for the test system.
7. The MIC is the minimum level of active ingredient necessary for the complete inhibition of growth of the test system. The MIC was recorded as the lowest concentration at which no turbidity (growth) was visually detected in the tube. If all tubes in a series were turbid, and it was not possible to determine whether the turbidity was due to bacterial growth or the handsoap itself, then those tubes were subcultured to an appropriate growth medium to determine the Minimum Bactericidal Concentration (MBC). The MBC is defined as the lowest concentration that demonstrated no survivors.

| METHOD PARAMETERS: Sample Identification: | | |
|---|---|---|
| Label | Test Substance | Active Ingredient |
| A | Endure ™ 100 | 0.2% Trichlosan |
| B | Bacti-Stat ™ Plus | 1% Triclosan |
| C | Scrub Stat ™ | 4% Chlorhexidine Gluconate |
| D | Cida ™ Rinse Gel | 70% Ethanol |
| E | Endure ™ 500 | 0.3% Trichlosan |

| | |
|---|---|
| Concentrations: | 1:2 through 1:131, 072 |
| Test systems: | *Staphylococcus aureus* ATCC 6538 |
| | *Escherichia coli* ATCC 11229 |
| | Methicillin Resistant |
| | *Staphylococcus aureus* HL 121 |
| MIC Subculture Medium: | AOAC Nutrient Broth |
| MBC Subculture Medium: | Tryptone Glucose Extract Agar (TGE) |
| Test Temperature: | Ambient (22–26° C.) |
| Subculture Method: | Streak Plate Technique |
| Incubation: | 37° C. for 24 hours (MIC) |
| | 37° C. for 48 hours (MBC) |

| RESULTS: MIC Values of Individual Organisms for Each Product Inoculum Numbers (CFU/mL) | | | |
|---|---|---|---|
| Test System | A | B | Average |
| *Staphylococcus aureus* ATCC 6538 | 37 × $10^6$ | 18 × $10^6$ | 2.8 × $10^7$ |
| *Escherichia coli* ATCC 11229 | 60 × $10^6$ | 78 × $10^6$ | 6.9 × $10^7$ |

-continued

| Methicillin Resistant *Staphylococcus aureus* HL 121 | 8 × $10^6$ | 15 × $10^6$ | 1.2 × $10^7$ |
|---|---|---|---|

| *Staphylococcus aureus* ATCC 6538 | | | | | |
|---|---|---|---|---|---|
| Test Substance Dilution | Endure ™ 100 | Bacti-Stat ™ Plus | Scrub Stat ™ | Cida ™ Rinse Gel | Endure ™ 500 |
| 1:2 | o | o | o | o | o |
| 1:4 | o | o | o | o | o |
| 1:8 | o | o | o | + | o |
| 1:16 | o | o | o | + | o |
| 1:32 | o | o | o | + | o |
| 1:64 | o | o | o | + | o |
| 1:128 | o | o | o | + | o |
| 1:256 | o | o | o | + | o |
| 1:512 | o | o | o | + | o |
| 1:1024 | o | o | o | + | o |
| 1:2048 | o | o | o | + | o |
| 1:4096 | o | o | o | + | o |
| 1:8192 | o | o | o | + | o |
| 1:16,384 | o | o | o | + | o |
| 1:32,768 | o | + | o | + | o |
| 1:65,536 | + | + | + | + | + |
| 1:131,072 | + | + | + | + | + |
| 1:262,144 | + | + | + | + | + |

| *Escherichia coli* ATCC 11229 | | | | | |
|---|---|---|---|---|---|
| Test Substance Dilution | Endure ™ 100 | Bacti-Stat ™ Plus | Scrub Stat ™ | Cida ™ Rinse Gel | Endure ™ 500 |
| 1:2 | o | o | o | o | o |
| 1:4 | o | o | o | o | o |
| 1:8 | o | o | o | o | o |
| 1:16 | o | o | o | + | o |
| 1:32 | o | o | o | + | o |
| 1:64 | o | o | o | + | o |
| 1:128 | o | o | o | + | o |
| 1:256 | o | o | o | + | o |
| 1:512 | o | o | o | + | o |
| 1:1024 | o | o | o | + | o |
| 1:2048 | o | o | o | + | o |
| 1:4096 | o | o | o | + | o |
| 1:8192 | o | o | o | + | o |
| 1:16,384 | o | o | o | + | o |
| 1:32,768 | + | o | o | + | + |
| 1:65,536 | + | o | + | + | + |
| 1:131,072 | + | o | + | + | + |
| 1:262,144 | + | + | + | + | + |

-continued

Methicillin Resistant *Staphylococcus aureus* HL 121

| Test Substance Dilution | Endure™ 100 | Bacti-Stat™ Plus | Scrub Stat™ | Cida™ Rinse Gel | Endure™ 500 |
|---|---|---|---|---|---|
| 1:2 | o | O | O | O | O |
| 1:4 | o | O | O | O | O |
| 1:8 | o | O | O | (O) | O |
| 1:16 | o | O | O | + | O |
| 1:32 | o | O | O | + | O |
| 1:64 | o | O | O | + | O |
| 1:128 | o | O | O | + | O |
| 1:256 | o | O | O | + | O |
| 1:512 | o | O | O | + | O |
| 1:1024 | o | O | O | + | O |
| 1:2048 | o | O | O | + | O |
| 1:4096 | o | O | O | + | O |
| 1:8192 | o | O | O | + | O |
| 1:16,384 | o | O | O | + | O |
| 1:32,768 | (o) | (O) | (O) | + | (O) |
| 1:65,536 | + | + | + | + | + |
| 1:131,072 | + | + | + | + | + |
| 1:262,144 | + | + | + | + | + |

Skin Synergy: Inoculum Numbers (CFU/mL) B + C, B + E, C + E

| Test System | A | B | Average |
|---|---|---|---|
| *Staphylococcus aureus* ATCC 6538 | $23 \times 10^6$ | $26 \times 10^6$ | $2.5 \times 10^7$ |
| *Escherichia coli* ATCC 11229 | $31 \times 10^6$ | $42 \times 10^6$ | $3.7 \times 10^7$ |
| Methicillin Resistant *Staphylococcus aureus* HL 121 | $13 \times 10^6$ | $23 \times 10^6$ | $1.8 \times 10^7$ |

Inoculum Numbers (CFU/mL) B + D, C + D

| Test System | A | B | Average |
|---|---|---|---|
| *Staphylococcus aureus* ATCC 6538 | $7 \times 10^7$ | $30 \times 10^7$ | $1.9 \times 10^8$ |
| *Escherichia coli* ATCC 11229 | $88 \times 10^6$ | $124 \times 10^6$ | $1.1 \times 10^8$ |
| Methicillin Resistant *Staphylococcus aureus* HL 121 | $16 \times 10^6$ | $18 \times 10^6$ | $1.7 \times 10^7$ |

Inoculum Numbers (CFU/mL) A + B, A + C, A + D

| Test System | A | B | Average |
|---|---|---|---|
| *Staphylococcus aureus* ATCC 6538 | $67 \times 10^6$ | $62 \times 10^6$ | $6.5 \times 10^7$ |
| *Escherichia coli* ATCC 11229 | $15 \times 10^7$ | $13 \times 10^7$ | $1.4 \times 10^8$ |
| Methicillin Resistant *Staphylococcus aureus* HL 121 | $17 \times 10^6$ | $20 \times 10^6$ | $1.9 \times 10^7$ |

Inoculum Numbers (CFU/mL) A + E, D + E

| Test System | A | B | Average |
|---|---|---|---|
| *Staphylococcus aureus* ATCC 6538 | $19 \times 10^6$ | $20 \times 10^6$ | $2.0 \times 10^7$ |
| *Escherichia coli* ATCC 11229 | $16 \times 10^7$ | $16 \times 10^7$ | $1.6 \times 10^8$ |
| Methicillin Resistant *Staphylococcus aureus* HL 121 | $15 \times 10^6$ | $15 \times 10^6$ | $1.5 \times 10^7$ |

*Staphylococcus aureus* ATCC 6538: A + B Combination

| Test Substance Combination | 100% B | 80% B | 60% B | 40% B | 20% B | 0% B |
|---|---|---|---|---|---|---|
| 100% A | o | o | o | o | o | (o) |
| 80% A | o | o | o | o | o | (o) |
| 60% A | o | o | o | o | o | (o) |
| 40% A | o | o | o | (o) | + | + |
| 20% A | o | o | (o) | + | + | + |
| 0% A | o | (o) | + | + | + | + |

*Escherichia coli* ATCC 11229: A + B Combination

| Test Substance Combination | 100% B | 80% B | 60% B | 40% B | 20% B | 0% B |
|---|---|---|---|---|---|---|
| 100% A | o | o | o | o | (o) | + |
| 80% A | o | o | o | (o) | + | + |
| 60% A | o | o | (o) | + | + | + |
| 40% A | o | o | (o) | + | + | + |
| 20% A | o | (o) | + | + | + | + |
| 0% A | (o) | + | + | + | + | + |

Methicillin Resistant *Staphylococcus aureus* HL 121: A + B Combination

| Test Substance Combination | 100% B | 80% B | 60% B | 40% B | 20% B | 0% B |
|---|---|---|---|---|---|---|
| 100% A | o | o | o | o | o | (o) |
| 80% A | o | o | o | o | o | (o) |
| 60% A | o | o | o | o | o | (o) |
| 40% A | o | o | o | o | o | (o) |
| 20% A | o | o | (o) | + | + | + |
| 0% A | o | o | (o) | + | + | + |

*Staphylococcus aureus* ATCC 6538: A + C Combination

| Test Substance Combination | 100% C | 80% C | 60% C | 40% C | 20% C | 0% C |
|---|---|---|---|---|---|---|
| 100% A | o | o | o | o | o | (o) |
| 80% A | o | o | o | o | o | (o) |
| 60% A | o | o | o | o | o | (o) |
| 40% A | o | o | o | o | (o) | + |
| 20% A | o | o | o | (o) | + | + |
| 0% A | o | o | (o) | + | + | + |

Escherichia coli ATCC 11229: A + C Combination

| Test Substance Combination | 100% C | 80% C | 60% C | 40% C | 20% C | 0% C |
|---|---|---|---|---|---|---|
| 100% A | o | o | o | o | o | ▓ |
| 80% A | o | o | o | o | ▓ | + |
| 60% A | o | o | o | o | ▓ | + |
| 40% A | o | o | o | ▓ | + | + |
| 20% A | o | o | ▓ | + | + | + |
| 0% A | o | ▓ | + | + | + | + |

Methicillin Resistant Staphylococcus aureus HL 121: A + C Combination

| Test Substance Combination | 100% C | 80% C | 60% C | 40% C | 20% C | 0% C |
|---|---|---|---|---|---|---|
| 100% A | o | o | o | o | o | ▓ |
| 80% A | o | o | o | o | o | ▓ |
| 60% A | o | o | o | o | o | ▓ |
| 40% A | o | o | o | o | ▓ | + |
| 20% A | o | o | ▓ | + | + | + |
| 0% A | o | o | ▓ | + | + | + |

Staphylococcus aureus ATCC 6538: A + D Combination

| Test Substance Combination | 100% D | 80% D | 60% D | 40% D | 20% D | 0% D |
|---|---|---|---|---|---|---|
| 100% A | o | o | o | o | o | ▓ |
| 80% A | o | o | o | o | o | ▓ |
| 60% A | o | o | ▓ | + | + | + |
| 40% A | ▓ | + | + | + | + | + |
| 20% A | + | + | + | + | + | + |
| 0% A | + | + | + | + | + | + |

Escherichia coli ATCC 11229: A + D Combination

| Test Substance Combination | 100% D | 80% D | 60% D | 40% D | 20% D | 0% D |
|---|---|---|---|---|---|---|
| 100% A | o | o | o | o | o | ▓ |
| 80% A | + | + | + | + | + | + |
| 60% A | + | + | + | + | + | + |
| 40% A | + | + | + | + | + | + |
| 20% A | + | + | + | + | + | + |
| 0% A | + | + | + | + | + | + |

Methicillin Resistant Staphylococcus aureus HL 121: A + D Combination

| Test Substance Combination | 100% D | 80% D | 60% D | 40% D | 20% D | 0% D |
|---|---|---|---|---|---|---|
| 100% A | o | o | o | o | o | ▓ |
| 80% A | o | o | o | o | o | ▓ |
| 60% A | o | o | ▓ | + | o | + |
| 40% A | o | ▓ | + | + | + | + |
| 20% A | + | + | + | + | + | + |
| 0% A | + | + | + | + | + | + |

Staphylococcus aureus ATCC 6538: A + E Combination

| Test Substance Combination | 100% E | 80% E | 60% E | 40% E | 20% E | 0% E |
|---|---|---|---|---|---|---|
| 100% A | o | o | o | o | o | ▓ |
| 80% A | o | o | ▓ | + | + | + |
| 60% A | o | ▓ | + | + | + | + |
| 40% A | ▓ | + | + | + | + | + |
| 20% A | + | + | + | + | + | + |
| 0% A | + | + | + | + | + | + |

Escherichia coli ATCC 11229: A + E Combination

| Test Substance Combination | 100% E | 80% E | 60% E | 40% E | 20% E | 0% E |
|---|---|---|---|---|---|---|
| 100% A | o | o | o | o | o | ▓ |
| 80% A | o | o | o | o | o | ▓ |
| 60% A | o | o | o | o | o | ▓ |
| 40% A | o | o | o | ▓ | + | + |
| 20% A | o | ▓ | + | + | + | + |
| 0% A | o | ▓ | + | + | + | + |

Methicillin Resistant Staphylococcus aureus HL 121: A + E Combination

| Test Substance Combination | 100% E | 80% E | 60% E | 40% E | 20% E | 0% E |
|---|---|---|---|---|---|---|
| 100% A | o | o | o | o | o | ▓ |
| 80% A | + | + | + | + | + | + |
| 60% A | + | + | + | + | + | + |
| 40% A | + | + | + | + | + | + |
| 20% A | + | + | + | + | + | + |
| 0% A | + | + | + | + | + | + |

Staphylococcus aureus ATCC 6538: B + C Combination

| Test Substance Combination | 100% C | 80% C | 60% C | 40% C | 20% C | 0% C |
|---|---|---|---|---|---|---|
| 100% B | o | o | o | o | o | ▓ |
| 80% B | o | o | o | o | o | ▓ |
| 60% B | o | o | o | o | o | ▓ |
| 40% B | o | o | o | o | ▓ | + |
| 20% B | o | o | o | ▓ | + | + |
| 0% B | o | o | ▓ | + | + | + |

-continued

Escherichia coli ATCC 11229: B + C Combination

| Test Substance Combination | 100% C | 80% C | 60% C | 40% C | 20% C | 0% C |
|---|---|---|---|---|---|---|
| 100% B | o | o | o | o | o | ▒ |
| 80% B  | o | o | o | o | ▒ | + |
| 60% B  | o | o | o | ▒ | + | + |
| 40% B  | o | o | o | ▒ | + | + |
| 20% B  | o | o | ▒ | + | + | + |
| 0% B   | ▒ | + | + | + | + | + |

Methicillin Resistant Staphylococcus aureus HL 121: B + C Combination

| Test Substance Combination | 100% C | 80% C | 60% C | 40% C | 20% C | 0% C |
|---|---|---|---|---|---|---|
| 100% B | o | o | o | o | o | ▒ |
| 80% B  | o | o | o | o | o | ▒ |
| 60% B  | o | o | o | o | o | ▒ |
| 40% B  | o | o | o | o | o | ▒ |
| 20% B  | o | o | o | o | o | ▒ |
| 0% B   | o | o | o | ▒ | + | + |

Staphylococcus aureus ATCC 6538: B + D Combination

| Test Substance Combination | 100% D | 80% D | 60% D | 40% D | 20% D | 0% D |
|---|---|---|---|---|---|---|
| 100% B | o | o | o | o | o | ▒ |
| 80% B  | o | o | o | o | o | ▒ |
| 60% B  | o | o | o | o | o | ▒ |
| 40% B  | o | o | o | o | ▒ | + |
| 20% B  | o | o | o | o | ▒ | + |
| 0% B   | o | o | o | ▒ | + | + |

Escherichia coli ATCC 11229: B + D Combination

| Test Substance Combination | 100% D | 80% D | 60% D | 40% D | 20% D | 0% D |
|---|---|---|---|---|---|---|
| 100% B | o | o | o | o | o | ▒ |
| 80% B  | o | o | o | ▒ | + | + |
| 60% B  | o | o | o | ▒ | + | + |
| 40% B  | o | o | ▒ | + | + | + |
| 20% B  | o | ▒ | + | + | + | + |
| 0% B   | o | ▒ | + | + | + | + |

Methicillin Resistant Staphylococcus aureus HL 121: B + D Combination

| Test Substance Combination | 100% D | 80% D | 60% D | 40% D | 20% D | 0% D |
|---|---|---|---|---|---|---|
| 100% B | o | o | o | o | o | ▒ |
| 80% B  | o | o | o | o | o | ▒ |
| 60% B  | o | o | o | o | o | ▒ |
| 40% B  | o | o | o | o | o | ▒ |
| 20% B  | o | o | o | o | ▒ | + |
| 0% B   | o | o | o | ▒ | + | + |

Staphylococcus aureus ATCC 6538: B + E Combination

| Test Substance Combination | 100% E | 80% E | 60% E | 40% E | 20% E | 0% E |
|---|---|---|---|---|---|---|
| 100% B | o | o | o | o | o | ▒ |
| 80% B  | o | o | o | o | o | ▒ |
| 60% B  | + | + | o | + | + | + |
| 40% B  | + | + | + | + | + | + |
| 20% B  | + | + | + | + | + | + |
| 0% B   | + | + | + | + | + | + |

Escherichia coli ATCC 11229: B + E Combination

| Test Substance Combination | 100% E | 80% E | 60% E | 40% E | 20% E | 0% E |
|---|---|---|---|---|---|---|
| 100% B | o | o | o | o | ▒ | + |
| 80% B  | o | o | o | o | ▒ | + |
| 60% B  | o | o | o | ▒ | + | + |
| 40% B  | o | o | o | ▒ | + | + |
| 20% B  | o | o | o | ▒ | + | + |
| 0% B   | o | o | ▒ | + | + | + |

Methicillin Resistant Staphylococcus aureus HL 121: B + E Combination

| Test Substance Combination | 100% E | 80% E | 60% E | 40% E | 20% E | 0% E |
|---|---|---|---|---|---|---|
| 100% B | o | o | o | o | o | ▒ |
| 80% B  | o | o | o | o | o | ▒ |
| 60% B  | o | o | o | o | ▒ | + |
| 40% B  | o | o | o | o | ▒ | + |
| 20% B  | o | o | o | o | ▒ | + |
| 0% B   | o | o | o | ▒ | + | + |

-continued

*Staphylococcus aureus* ATCC 6538: C + D Combination

| Test Substance Combination | 100% D | 80% D | 60% D | 40% D | 20% D | 0% D |
|---|---|---|---|---|---|---|
| 100% C | o | o | o | o | o | ■ |
| 80% C  | o | o | o | o | o | ■ |
| 60% C  | o | o | o | o | o | ■ |
| 40% C  | o | o | o | o | ■ | + |
| 20% C  | o | o | ■ | + | + | + |
| 0% C   | o | ■ | + | + | + | + |

*Escherichia coli* ATCC 11229: C + D Combination

| Test Substance Combination | 100% D | 80% D | 60% D | 40% D | 20% D | 0% D |
|---|---|---|---|---|---|---|
| 100% C | o | o | o | o | ■ | + |
| 80% C  | o | o | o | o | ■ | + |
| 60% C  | o | o | o | ■ | + | + |
| 40% C  | o | o | o | ■ | + | + |
| 20% C  | o | o | ■ | + | + | + |
| 0% C   | o | o | ■ | + | + | + |

Methicillin Resistant *Staphylococcus aureus* HL 121: C + D Combination

| Test Substance Combination | 100% D | 80% D | 60% D | 40% D | 20% D | 0% D |
|---|---|---|---|---|---|---|
| 100% C | o | o | o | o | o | ■ |
| 80% C  | o | o | o | o | o | ■ |
| 60% C  | o | o | o | o | o | ■ |
| 40% C  | o | o | o | o | o | ■ |
| 20% C  | o | o | o | o | ■ | + |
| 0% C   | o | o | o | ■ | + | + |

*Staphylococcus aureus* ATCC 6538: C + E Combination

| Test Substance Combination | 100% E | 80% E | 60% E | 40% E | 20% E | 0% E |
|---|---|---|---|---|---|---|
| 100% C | o | o | o | o | o | ■ |
| 80% C  | o | o | o | o | o | ■ |
| 60% C  | o | o | o | o | o | ■ |
| 40% C  | o | o | o | o | ■ | + |
| 20% C  | o | o | o | o | ■ | + |
| 0% C   | ■ | + | o | + | + | + |

*Escherichia coli* ATCC 11229: C + E Combination

| Test Substance Combination | 100% E | 80% E | 60% E | 40% E | 20% E | 0% E |
|---|---|---|---|---|---|---|
| 100% C | o | o | o | o | o | ■ |
| 80% C  | o | o | o | o | o | ■ |
| 60% C  | o | o | o | o | ■ | + |
| 40% C  | o | o | o | ■ | + | + |
| 20% C  | o | o | ■ | + | + | + |
| 0% C   | o | o | ■ | + | + | + |

Methicillin Resistant *Staphylococcus aureus* HL 121: C + E Combination

| Test Substance Combination | 100% E | 80% E | 60% E | 40% E | 20% E | 0% E |
|---|---|---|---|---|---|---|
| 100% C | o | o | o | o | o | ■ |
| 80% C  | o | o | o | o | o | ■ |
| 60% C  | o | o | o | o | o | ■ |
| 40% C  | o | o | o | o | o | ■ |
| 20% C  | o | o | o | o | ■ | + |
| 0% C   | o | o | o | o | ■ | + |

*Staphylococcus aureus* ATCC 6538: D + E Combination

| Test Substance Combination | 100% E | 80% E | 60% E | 40% E | 20% E | 0% E |
|---|---|---|---|---|---|---|
| 100% D | o | o | o | o | o | ■ |
| 80% D  | o | o | o | o | o | ■ |
| 60% D  | o | o | o | o | o | ■ |
| 40% D  | o | o | o | ■ | + | + |
| 20% D  | o | o | ■ | + | + | + |
| 0% D   | o | ■ | + | + | + | + |

*Escherichia coli* ATCC 11229: D + E Combination

| Test Substance Combination | 100% E | 80% E | 60% E | 40% E | 20% E | 0% E |
|---|---|---|---|---|---|---|
| 100% D | o | o | o | o | o | ■ |
| 80% D  | o | o | o | o | o | ■ |
| 60% D  | o | o | o | ■ | + | o |
| 40% D  | o | o | o | ■ | + | + |
| 20% D  | o | o | ■ | + | + | + |
| 0% D   | o | o | ■ | + | + | + |

-continued

Methicillin Resistant *Staphylococcus aureus* HL 121:
D + E Combination

| Test Substance Combination | 100% E | 80% E | 60% E | 40% E | 20% E | 0% E |
|---|---|---|---|---|---|---|
| 100% D | o | o | o | o | o | ▓ |
| 80% D | o | o | o | o | o | ▓ |
| 60% D | o | o | o | o | o | ▓ |
| 40% D | o | o | o | o | o | ▓ |
| 20% D | o | o | o | ▓ | + | + |
| 0% D | o | o | o | ▓ | + | + |

Conclusions

General conclusions were drawn using all organism data:

Endure™ 100, in combination with Bacti-Stat™ Plus demonstrated synergy. Therefore, 0.2% Triclosan and 1% Triclosan demonstrated synergy. Endure™ 100, in combination with Scrub Stat™ 4 demonstrated synergy. Therefore, 0.2% Triclosan and 4% Chlorhexidine Gluconate demonstrated synergy. Endure™ 100, in combination with Cida-Rinse™ Gel demonstrated synergy. Therefore, 0.2% Triclosan and 70% Ethanol demonstrated synergy. Endure™ 100, in combination with Endure™ 500 demonstrated neither synergy nor antagonism. Therefore, 0.2% Triclosan and 0.3% Triclosan demonstrated neither synergy nor antagonsim.

Bacti-Stat™ Plus, in combination with Scrub Stat™ 4 demonstrated synergy. Therefore, 1% Triclosan and 4% Chlorhexidine Gluconate demonstrated synergy. Bacti-Stat Plus™, in combination with Cida-Rinse™ Gel demonstrated synergy. Therefore, 1% Triclosan and 70% Ethanol demonstrated synergy. Bacti-Stat™ Plus, in combination with Endure™ 500 demonstrated synergy. Therefore, 1% Triclosan and 0.3% Triclosan demonstrated synergy.

Scrub Stat™ 4, in combination with Cida-Rinse™ Gel demonstrated synergy. Therefore, 4% Chlorhexidine Gluconate and 70% Ethanol demonstrated synergy. Scrub Stat™ 4, in combination with Endure™ 500 demonstrated synergy. Therefore, 4% Chlorhexidine Gluconate and 0.3% Triclosan demonstrated synergy.

Cida-Rinse™ Gel, in combination with Endure™ 500 demonstrated synergy. Therefore, 70% Ethanol and 0.3% Triclosan demonstrated synergy.

The above data from the examples are compelling evidence that not all possible combinations of antimicrobial skin treatments will provide synergistic interaction, and that the specific combinations recited in the description of the present invention do provide significant synergistic antimicrobial activity. For example, the combination of 0.2% Triclosan and 0.3% Triclosan wash compositions did not display synergy, while the combination of 0.1% Triclosan and 1% Triclosan did provide synergy, leading to the defined limitation of at least 0.1% in one composition and greater than 0.3%, at least 0.35%, at least 0.4%, or at least 0.5% in another composition as being a standard for synergy in Triclosan-only combinations of antimicrobial compositions (or combinations of two Tricolsan compositions with a third or fourth composition of other antimicrobial compounds). The combinations of Triclosan-only compositions may therefore comprise, for example, one Triclosan composition with at least 0.1% by weight of Triclosan and a second solution comprising greater than 0.3% Triclosan, such as at least 0.35% Triclosan, preferably at least 0.5% Triclosan, at least 0.7% Triclosan, at least 1.% Triclosan, and the like.

Each of the classes of synergistic compositions described as within the scope of the present invention has been reasonably demonstrated as exhibiting at least some synergistic activity when used in controlled environments. As noted before, the compositions may be provided in sets of materials that can be supplied to a consumer so that the various materials may be used at a single site within a location used by the consumer or at various distinct sites throughout a single location operated by the consumer. For example, kits or combined packages may be provided that have the various compositions in adjusted proportions within the kit or package. For example, in a medical treatment environment, the package may contain one or more of a general purpose antimicrobial wash composition, an antimicrobial skin treatment composition, an antimicrobial pediatric wash composition, an antimicrobial wash for isolation areas, an antimicrobial pre-surgery pre-scrub composition, an antimicrobial post-surgery wash composition, and an antimicrobial post-work wash composition (to prevent microbes from being carried away from the medical environment). Based upon the inventive compositions, and assuming, for purposes of exemplification only, that the composition general purpose lavatory-available wash solution or composition is a liquid or bar soap composition comprising at least 0.1% Triclosan, that general purpose composition would be provided in volumes that are multiples of the other materials provided. Given the desire to provide a combination of materials selected from the group consisting of:

a) one washing solution comprising Triclosan and another washing solution comprising chlorhexidine gluconate;

b) two washing solutions comprising at least 0.1% Triclosan and at least one of said two washing solutions comprising greater than 0.3% Triclosan; and c) one washing solution comprising Triclosan and another washing solution comprising an alcohol (e.g., ethanol, isopropanol);

or more generally a washing station having at least two washing compositions available for use, one washing solution comprising at least 0.1% by weight of Triclosan and another washing solution being selected from the group consisting of:

a) a washing composition or solution comprising chlorhexidine gluconate;

b) a washing solution or composition comprising Triclosan comprising greater than 0.3% Triclosan; and c) a washing solution or composition comprising an alcohol (e.g., ethanol, or isopropanol);

the kit or package could contain five units (e.g., 5 liters) of the general wash composition, two units (e.g., 2 liters) of the pediatric scrub composition, three units of the skin treatment composition, one unit of the surgical prescrub composition, and two units of the post-surgical wash composition. Therefore, one of the formats for presentation of the compositions of the present invention would comprise a kit or package containing at least two compositions which interact in a synergistic relationship for antimicrobial effects (the combination of the at least two compositions being referred to herein to as a synergistic composition), the proportions of one of the two compositions that forms the synergistic composition being present in an amount which is at least twice, at least three times, at least four times, or at least five times the volume of a second of the compositions that forms the synergistic composition. For example, the package may contain ten units a general wash solution with at least about 0.1% Triclosan, and at least one unit, but less than five units of at least one, at least two, at least three, at least four, or at least five different antimicrobial compositions, each of which (or at least some of which) from synergistic combinations with the general wash composition). One format might therefore comprise a package having at least ten units (e.g., where provided as a liquid, the most likely format of provision, the units would be by volume) of a general wash composition or special wash composition comprising at least 0.1% Triclosan, and at least one additional composition in an amount less than ten units, the additional composition comprising less than ten units of at least one and up to even ten variations of one or more compositions comprising:

a) a washing composition or solution comprising chlorhexidine gluconate;

b) a washing solution or composition comprising Triclosan comprising greater than 0.3% Triclosan; and c) a washing solution or composition comprising an alcohol (e.g., ethanol, or isopropanol).

What is claimed:

1. A method of providing a synergistic antimicrobial activity to skin or hair comprising applying to said skin or hair one composition comprising at least 0.1% by weight of Triclosan and another composition being selected from the group consisting of:

a) a composition comprising chlorhexidine gluconate;

b) a composition comprising Triclosan, in a different weight percentage of Triclosan than said one composition, comprising greater than 0.3% Triclosan;

c) a composition comprising an alcohol.

2. The method of claim 1 wherein the composition comprising at least 0.1% Triclosan is a first applied composition.

3. The method of claim 1 wherein the composition comprising at least 0.1% Triclosan is a second applied composition.

4. A method of providing a synergistic antimicrobial activity to skin or hair comprising applying to said skin or hair one composition comprising at least 0.1% by weight of antimicrobially active aliphatic phenol derivative and another composition being selected from the group consisting of:

a) a solution comprising an antimicrobially active cationic species;

b) a comprising antimicrobially active aliphatic phenol derivative, preferably in a different weight percentage of antimicrobially active aliphatic phenol derivative than said one composition, comprising greater than 0.3% antimicrobially active aliphatic phenol derivative;

c) a solution comprising an alcohol.

* * * * *